United States Patent [19]

Wolf et al.

[11] Patent Number: 5,256,632
[45] Date of Patent: Oct. 26, 1993

[54] HERBICIDAL SULPHONYLATED CARBOXAMIDES

[75] Inventors: Hilmar Wolf, Langenfeld; Rolf Kirsten, Monheim; Hans-Joachim Santel, Leverkusen; Klaus Lürssen; Robert R. Schmidt, both of Gladbach, Fed. Rep. of Germany

[73] Assignee: Bayer Aktiengesellschaft, Leverkusen, Fed. Rep. of Germany

[21] Appl. No.: 900,867

[22] Filed: Jun. 18, 1992

Related U.S. Application Data

[63] Continuation-in-part of Ser. No. 704,544, May 23, 1991, Pat. No. 5,205,853.

[30] Foreign Application Priority Data

May 30, 1991 [DE] Fed. Rep. of Germany ....... 4017338
May 14, 1992 [DE] Fed. Rep. of Germany ....... 4215878

[51] Int. Cl.$^5$ ................. A01N 43/48; C07D 413/02; C07D 271/04; C07D 271/06
[52] U.S. Cl. ..................... 504/252; 504/253; 504/262; 504/263; 504/265; 504/266; 504/269; 504/270; 504/271; 546/275; 546/277; 546/280; 548/131; 548/132; 548/133; 548/136; 548/143; 548/144; 548/188; 548/194; 548/200; 548/236; 548/248; 548/214
[58] Field of Search ............... 548/248, 236, 131, 132, 548/133, 188, 194, 200, 143, 144, 136, 214; 71/88, 90, 92, 94; 504/252, 253, 262, 263, 265, 266, 269, 270, 271; 546/275, 277, 280

[56] References Cited

PUBLICATIONS

CA 115:256192m Preparation ... Herbicides Makino et al., p. 869, 1991.
CA 110:8204e Preparation ... Herbicides, Wellinga et al., p. 755, 1989.

*Primary Examiner*—Mary C. Lee
*Assistant Examiner*—Joseph K. McKane
*Attorney, Agent, or Firm*—Sprung Horn Kramer & Woods

[57] ABSTRACT

Herbicidal sulphonylated carboxamides of the formula $$R^1-CO-NH-SO_2-(A)_n-R^2 \qquad (I)$$

in which
  n represents the numbers 0 or 1,
  A represents oxygen, iminio (NH) or methylene (CH$_2$),
  $R^1$ represents a five-membered heteroaryl radical which contains 1 or 2 nitrogen atoms and additionally one oxygen or sulphur atom in the ring and which is optionally substituted by halogen or by alkyl, alkoxy, alkylthio, alkylsulphinyl, alkylsulphonyl, alkylamino, dialkylamino or phenyl which are in each case optionally substituted, and
  $R^2$ represents aryl or heteroaryl which are in each case optionally substituted, or salts thereof, with the exclusion of the compound 2-dimethylamino-N-(4-methyl-phenylsulphonyl)-5-thiazole carboxamide.

11 Claims, No Drawings

HERBICIDAL SULPHONYLATED CARBOXAMIDES

This is a continuation-in-part of application Ser. No. 704,544, filed May 23, 1991, now U.S. Pat. No. 5,205,853.

The invention relates to new sulphonylated carboxamides, processes for their preparation and their use as herbicides.

2-Dimethylamino-N-(4-methyl-phenylsulphonyl)-5-thiazole carboxamide is already known from the literature as an example of sulphonylated carboxamides (compare J. Org. Chem. 46 (1981), 2790-2793). However, nothing has been published about the biological properties of the general formula (I)

$$R^1-CO-NH-SO_2-(A)_n-R^2 \qquad (I)$$

in which
n represents the numbers 0 or 1,
A represents oxygen, imino (NH) or methylene ($CH_2$),
$R^1$ represents a five-membered heteroaryl radical which contains 1 or 2 nitrogen atoms and additionally one oxygen or sulphur atom in the ring and which is optionally substituted by halogen or by alkyl, alkoxy, alkylthio, alkylsulphinyl, alkylsulphonyl, alkylamino, dialkylamino or phenyl which are in each case optionally substituted, and
$R^2$ represents aryl or heteroaryl which are in each case optionally substituted, and salts of compounds of the formula (I) have now been found, the known 2-dimetylamino-N-(4-methyl-phenylsulphonyl)-5-thiazole carboxamide being excluded.

The new sulphonylated carboxamides of the formula (I) are obtained when (a) carboxamides of the general formula (II)

$$R^1-CO-NH_2 \qquad (II)$$

in which
$R^1$ has the above mentioned meaning,
are reacted with sulphonylating agents of the general formula (III)

$$X-SO_2-(A)_n-R^2 \qquad (III)$$

in which
n, A and $R^2$ have the abovementioned meanings and
X represents halogen,
if appropriate in the presence of an acid acceptor and if appropriate in the presence of a diluent, or when (b) carboxylic acids of the general formula (IV)

$$R^1-COOH \qquad (IV)$$

in which
$R^1$ has the abovementioned meaning, or reactive derivatives of carboxylic acids of the formula (IV)
are reacted with aminosulphonyl compounds of the general formula (V)

$$H_2N-SO_2-(A)_n-R^2 \qquad (V)$$

in which
n, A and $R^2$ have the abovementioned meanings,
or with reactive derivatives of the compounds of the formula (V)
if appropriate in the presence of reaction auxiliaries and if appropriate in the presence of diluents and, if appropriate, the products obtained by processes (a or (b) are converted into salts by customary methods.

The new sulphonylated carboxamides of the general formula (I) are distinguished by strong herbicidal activity.

The invention preferably relates to sulphonylated carboxamides of the formula (I) in which
n represents the numbers 0 or 1,
A represents oxygen, imino (NH) or methylene ($CH_2$),
$R^1$ represents a five-membered heteroaryl radical from the series comprising oxazolyl, isoxazolyl, thiazolyl, isothiazolyl, oxadiazolyl and thiadiazolyl, which is optionally monosubstituted or polysubstituted, in particular monosubstituted or disubstituted, by identical or different halogen or by optionally halogen-substituted $C_1$-$C_6$-alkyl, phenyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-alkylamino or di-($C_1$-$C_6$-alkyl)-amino, and
$R^2$ represents the radical

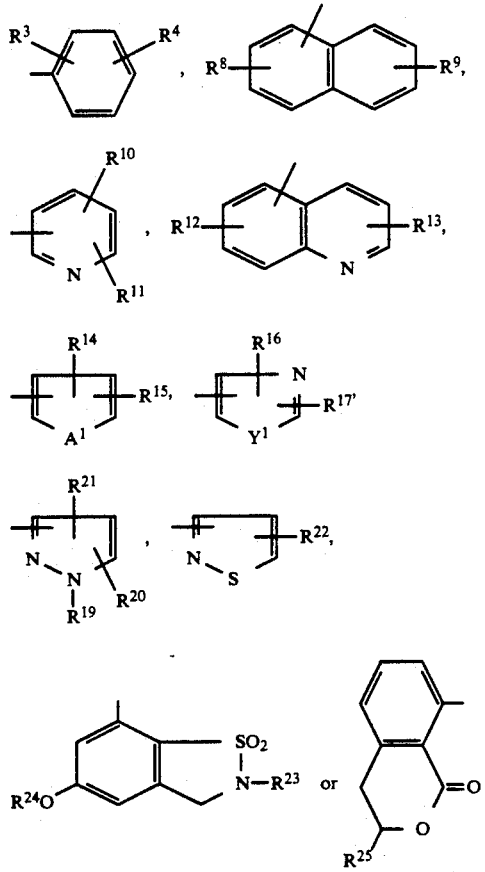

in which
$R^3$ and $R^4$ are identical or different and represent hydrogen, fluorine, chlorine, bromine, iodine, cyano, nitro, carboxyl or $C_1$-$C_6$-alkyl which is optionally substituted by fluorine, chlorine, bromine, cyano, carboxyl, $C_1$-$C_4$-alkoxycarbonyl, $C_1$-$C_4$-alkylamino-carbonyl, di-($C_1$-$C_4$-alkyl)aminocarbonyl, hydroxyl, $C_1$-$C_4$-alkoxy, formyloxy, $C_1$-$C_4$-alkyl-carbonyloxy, $C_1$-$C_4$-alkoxycarbonyloxy, $C_1$-$C_4$-alkylamino-carbonyloxy, $C_1$-$C_4$-alkylthio, $C_1$-$C_4$-alkylsulphinyl, $C_1$-$C_4$-alkylsulphonyl, di-($C_1$-$C_4$-alkyl)aminosulphonyl, $C_3$-$C_6$-cycloalkyl or phenyl, or $R^3$ and $R^4$ furthermore independently of one another represent $C_2$-$C_6$-alkenyl which is optionally substituted by fluorine, chlorine, bromine, cyano, $C_1$-$C_4$-alkoxycarbonyl, carboxyl or phenyl, or $R^3$ and $R^4$ additionally independently of one another represent $C_2$-$C_6$-alkinyl which is optionally substituted by fluorine, chlorine, bromine, cyano, $C_1$-$C_4$-alkoxy-carbonyl, carboxyl or phenyl; $C_1$-$C_4$-alkoxy which is optionally substituted by fluorine, chlorine, bromine, cyano, carboxyl, $C_1$-$C_4$-alkoxycarbonyl, $C_1$-$C_4$-alkoxy, $C_1$-$C_4$-alkylthio, $C_1$-$C_4$-alkylsulphinyl or $C_1$-$C_4$-alkylsulphonyl; $C_1$-$C_4$-alkylthio which is optionally substituted by fluorine, chlorine, bromine, cyano, carboxyl, $C_1$-$C_4$-alkoxycarbonyl, $C_1$-$C_4$-alkylthio, $C_1$-$C_4$-alkylsulphinyl or $C_1$-$C_4$-alkylsulphonyl; $C_3$-$C_6$-alkenyloxy which is optionally substituted by fluorine, chlorine, bromine, cyano or $C_1$-$C_4$-alkoxy-carbonyl, $C_2$-$C_6$-alkenylthio which is optionally substituted by fluorine, chlorine, bromine, cyano, nitro, $C_1$-$C_3$-alkylthio or $C_1$-$C_4$-alkoxycarbonyl; $C_3$-$C_6$-alkynyloxy, $C_3$-$C_6$-alkynylthio or the radical —$S(O)_p$—$R^5$, or $R^3$ and $R^4$ furthermore represent phenyl or phenoxy, $C_1$-$C_4$-alkylcarbonylamino, $C_1$-$C_4$-alkoxycarbonylamino, $C_1$-$C_4$-alkylamino-carbonylamino, di-($C_1$-$C_4$-alkyl)-amino-carbonylamino, or the radical —CO—$R^6$, or $R^3$ and $R^4$ furthermore represent $C_1$-$C_4$-alkylsulphonyloxy, di-($C_1$-$C_4$-alkyl)-aminosulphonylamino or the radical —CH=N—$R^7$, in which p represents the numbers 1 or 2 and $R^5$ represents $C_1$-$C_4$-alkyl which is optionally substituted by fluorine, chlorine, bromine, cyano or $C_1$-$C_4$-alkoxycarbonyl or $R^5$ represents $C_1$-$C_4$-alkoxy, $C_1$-$C_4$-alkoxy-$C_1$-$C_4$-alkylamino or di($C_1$-$C_4$-alkyl)-amino, $R^6$ represents $C_1$-$C_6$-alkyl, $C_1$-$C_6$-alkoxy which is optionally substituted by fluorine, chlorine, methoxy or ethoxy; $C_3$-$C_6$-cycloalkoxy, $C_3$-$C_6$-alkenyloxy, $C_1$-$C_4$-alkylthio, amino, $C_1$-$C_4$-alkylamino, $C_1$-$C_4$-alkoxyamino, $C_1$-$C_4$-alkoxy-$C_1$-$C_4$-alkyl-amino or di-($C_1$-$C_4$-alkyl)amino which are optionally substituted by fluorine and/or chlorine and $R^7$ represents $C_1$-$C_6$-alkyl which is optionally substituted by fluorine, chlorine, cyano, carboxyl, $C_1$-$C_4$-alkoxy, $C_1$-$C_4$-alkylthio, $C_1$-$C_4$-alkylsulphinyl or $C_1$-$C_4$-alkylsulphonyl, benzyl which is optionally substituted by fluorine or chlorine, $C_3$-$C_6$-alkenyl or $C_3$-$C_6$-alk nyl which are optionally substituted by fluorine or chlorine, phenyl which is optionally substituted by fluorine, chlorine, bromine, $C_1$-$C_4$-alkyl, $C_1$-$C_4$-alkoxy, trifluoromethyl, trifluoromethoxy or trifluoromethylthio, $C_1$-$C_6$-alkoxy, $C_3$-$C_6$-alkenyloxy, $C_3$-$C_6$-alkynyloxy or benzyloxy which are optionally substituted by fluorine and/or chlorine, or $R^7$ furthermore represents amino, $C_3$-$C_4$-alkylamino, di-($C_1$-$C_4$-alkyl)-amino, phenylamino, $C_1$-$C_4$-alkyl-carbonylamino, $C_1$-$C_4$-alkoxy-carbonylamino, $C_1$-$C_4$-alkylsulphonylamino or phenyl sulphonylamino which is optionally substituted by fluorine, chlorine, bromine or methyl, $R^8$ and $R^9$ are identical or different and represent hydrogen, fluorine, chlorine, bromine, nitro, cyano, $C_1$-$C_4$-alkyl which is optionally substituted by fluorine and/or chlorine; or $C_1$-$C_4$-alkoxy which is optionally substituted by fluorine and/or chlorine;

$R^{10}$ and $R^{11}$ are identical or different and represent hydrogen, fluorine, chlorine, bromine, nitro, cyano, or $C_1$-$C_4$-alkyl which is optionally substituted by fluorine and/or chlorine; $C_2$-$C_4$-alkenyl which is optionally substituted by fluorine and/or chlorine, $C_1$-$C_4$-alkoxy which is optionally substituted by fluorine and/or chlorine, $C_1$-$C_4$-alkylthio, $C_1$-$C_4$-alkylsulphinyl or $C_1$-$C_4$-alkylsulphonyl which are optionally substituted by fluorine and/or chlorine; and di-($C_1$-$C_4$-alkyl)-aminosulphonyl, $C_1$-$C_4$-alkoxy-carbonyl, dimethylaminocarbonyl or dioxolanyl;

$R^{12}$ and $R^{13}$ are identical or different and represent hydrogen, fluorine, chlorine; bromine or $C_1$-$C_4$-alkyl which is optionally substituted by fluorine and/or chlorine; $C_1$-$C_4$-alkoxy which is optionally substituted by fluorine and/or chlorine; $C_1$-$C_4$-alkylthio, $C_1$-$C_4$-alkylsulphinyl or $C_1$-$C_4$-alkylsulphonyl which are optionally substituted by fluorine and/or chlorine; or di-($C_1$-$C_4$-alkyl)aminosulphonyl;

$R^{14}$ and $R^{15}$ are identical or different and represent hydrogen, fluorine, chlorine, bromine, cyano, nitro or $C_1$-$C_4$-alkyl which is optionally substituted by fluorine, chlorine, $C_1$-$C_4$-alkoxy and/or $C_1$-$C_4$-halogenoalkoxy; $C_1$-$C_4$-alkoxy which is optionally substituted by fluorine and/or chlorine; $C_1$-$C_4$-alkylthio, $C_1$-$C_4$-alkylsulphinyl or $C_1$-$C_4$-alkylsulphonyl which are optionally substituted by fluorine and/or chlorine, di-($C_1$-$C_4$-alkyl)-amino-sulphonyl or $C_1$-$C_4$-alkoxycarbonyl, and $A^1$ represents oxygen, sulphur or the group N—$Z^1$, in which $Z^1$ represents hydrogen or $C_1$-$C_4$-alkyl which is optionally substituted by fluorine, chlorine, bromine or cyano; $C_3$-$C_6$-cycloalkyl, benzyl or phenyl, phenyl optionally being substituted by fluorine, chlorine, bromine or nitro; $C_1$-$C_4$-alkylcarbonyl, $C_1$-$C_4$-alkoxy-carbonyl or di-($C_1$-$C_4$-alkyl)aminocarbonyl, $R^{16}$ and $R^{17}$ are identical or different and represent hydrogen, $C_1$-$C_4$-alkyl, halogen, $C_1$-$C_4$-alkoxycarbonyl, $C_1$-$C_4$-alkoxy or $C_1$-$C_4$-halogenoalkoxy, $Y^1$ represents sulphur or the group N—$R^{18}$, in which $R^{18}$ represents hydrogen or $C_1$-$C_4$-alkyl, $R^{19}$ represents hydrogen, $C_1$-$C_4$-alkyl, phenyl or (iso)quinolinyl, $R^{20}$ represents hydrogen, halogen, cyano, nitro or $C_1$-$C_4$-alkyl which is optionally substituted by fluorine and/or chlorine; $C_1$-$C_4$-alkoxy which is optionally substituted by fluorine and/or chlorine; dioxolanyl or $C_1$-$C_4$-alkoxy-carbonyl, $R^{21}$ represents hydrogen, halogen or $C_1$-$C_4$-alkyl, $R^{22}$ represents hydrogen, halogen, $C_1$-$C_4$-alkyl or $C_1$-$C_4$-alkoxy-carbonyl, $R^{23}$ represents $C_1$-$C_4$-alkyl, $R^{24}$ represents $C_1$-$C_4$-alkyl and $R^{25}$ represents hydrogen or methyl, excluding the compound 2-(dimethylamino)-N-[(4-methylphenyl)sulphonyl]-5-thiazole carboxamide.

The invention relates in particular to compounds of the formula (I) in which n represents the numbers 0 or 1, A represents oxygen, imino (NH) or methylene (CH$_2$), R$^1$ represents a five-membered heteroaryl radical from the series comprising oxazolyl, isoxazolyl, thiazolyl, 1,2,4-oxadiazolyl, 1,3,4-oxadiazolyl, 1,2,4-thiadiazolyl and 1,3,4-thiadiazolyl, which is optionally substituted by fluorine, chlorine, bromine, methyl, ethyl, propyl, isopropy, butyl, isobutyl, sec-butyl, tert-butyl, fluoromethyl, chloromethyl, difluoromethyl, dichloromethyl, trifluoromethyl, trichloromethyl, chlorofluoromethyl, chlorodifluoromethyl, fluorodichloromethyl, phenyl, methoxy, ethoxy, propoxy, isopropyloxy, difluoromethoxy, trifluoromethoxy, chlorodifluoromethoxy, methylthio, ethylthio, propylthio, isopropylthio, difluoromethylthio, trifluoromethylthio, chlorodifluoromethylthio, methylsulphinyl, ethylsulphinyl, propylsulphinyl, methylsulphonyl, ethylsulphonyl, propysulphonyl, methylamino, ethylamino, propylamino, isopropylamino and/or dimethylamino, and R$^2$ represents the radical

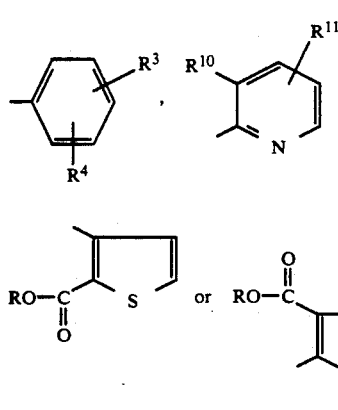

R$^3$ represents hydrogen, fluorine, chlorine, bromine, cyano, nitro, carboxyl, methyl, trifluoromethyl, methoxy, ethoxy, 2-chloroethoxy, difluoromethoxy, trifluoromethoxy, C$_1$–C$_3$-alkylthio, C$_1$–C$_3$-alkyl-sulphinyl, C$_1$–C$_3$-alkylsulphonyl, dimethylaminosulphonyl, diethylaminosulphonyl, N-methoxy-N-methylaminosulphonyl, phenyl, phenoxy or C$_1$–C$_3$-alkoxycarbonyl and R$^4$ represents hydrogen, fluorine, chlorine, bromine, methyl, trifluoromethyl or methoxy;

R$^{10}$ represents dimethylaminocarbonyl or C$_1$–C$_4$-alkylsulphonyl,

R$^{11}$ represents hydrogen, fluorine or chlorine and

R represents methyl or ethyl, excluding the compound 2-(dimethylamino)-N-[(4-methylphenyl)-sulphonyl]-5-thiazole carboxamide.

n in particular represents the number 0. If n represents the number 1, A in particular represents CH$_2$.

R$^2$ in particular represents

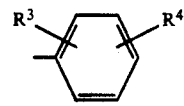

where R$^3$ and R$^4$ are preferably in the orthoposition.

R$^4$ in particular represents hydrogen.

The invention further preferably relates to salts of compounds of the formula (I) with bases, such as, for example, the hydroxide, hydride, amide or carbonate of sodium, potassium or calcium, C$_1$–C$_4$-alkoxides of sodium or potassium, ammonia, C$_1$–C$_4$-alkylamines, di-(C$_1$–C$_4$-alkyl)amines or tri-(C$_1$–C$_4$-alkyl)-amines.

Examples of the compounds of the formula (I) according to the invention are shown in Table 1 below.

$$R^1\text{—CO—NH—SO}_2\text{—(A)}_n\text{—R}^2 \quad (I)$$

TABLE 1

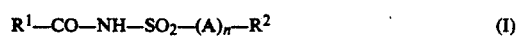

Examples of the compounds of the formula (I)

| R$^1$ | A | n | R$^2$ |
|---|---|---|---|
| H$_3$C–isoxazolyl | — | 0 | phenyl |
| H$_3$C–isoxazolyl | — | 0 | 4-CH$_3$-phenyl |
| H$_3$C–isoxazolyl | — | 0 | 2-CH$_3$-phenyl |
| H$_3$C–isoxazolyl | — | 0 | 4-Cl-phenyl |
| H$_3$C–isoxazolyl | — | 0 | 2-Cl-phenyl |
| H$_3$C–isoxazolyl | — | 0 | 2,3-di-Cl-phenyl |
| H$_3$C–isoxazolyl | — | 0 | 2,4-di-Cl-phenyl |

TABLE 1-continued
Examples of the compounds of the formula (I)
| R¹ | A | n | R² |
|---|---|---|---|
|  | — | 0 |  |
|  | — | 0 |  |
|  | — | 0 |  |
|  | — | 0 |  |
|  | — | 0 |  |
|  | — | 0 |  |
|  | — | 0 |  |
|  | — | 0 |  |
|  | — | 0 |  |
|  | — | 0 |  |

TABLE 1-continued
Examples of the compounds of the formula (I)

| R¹ | A | n | R² |
|---|---|---|---|
| [F₃C-C(=N-)-C(CH₃)=CH-O-N< isoxazole] | — | 0 | [phenyl-COOC₂H₅] |
| [H₃C-C(=N-)-C(CH₃)=CH-O-N< isoxazole] | — | 0 | [phenyl-CF₃] |
| [H₅C₂-C(=N-)-C(CH₃)=CH-O-N< isoxazole] | — | 0 | [phenyl-OCHF₂] |
| [Ph-C(=N-)-C(CH₃)=CH-N-O oxadiazole] | — | 0 | [phenyl-F] |
| [H₃C-C=CH-C(CH₃)=N-O isoxazole] | — | 0 | [phenyl-OCF₃] |
| [ClF₂C-C(=N-)-C(CH₃)=CH-O-N<] | — | 0 | [phenyl-Cl] |
| [(CH₃)₂CH-C(=N-)-C(CH₃)=CH-O-N<] | — | 0 | [phenyl-F, Cl] |
| [H₃C-C(=N)-CH=CH-O oxazole] | — | 0 | [phenyl-Cl, CH₃] |
| [H₃C-C(=N-)-CH=C(CH₃)-O-N isoxazole] | CH₂ | 1 | [phenyl-COOCH₃] |

If, for example, 2-trifluoromethyl-oxazole-4-carboxamide and 2-cyano-phenylmethanesulphonyl chloride are used as starting materials in process (a) according to the invention, the course of the reaction can be outlines by the following equation:

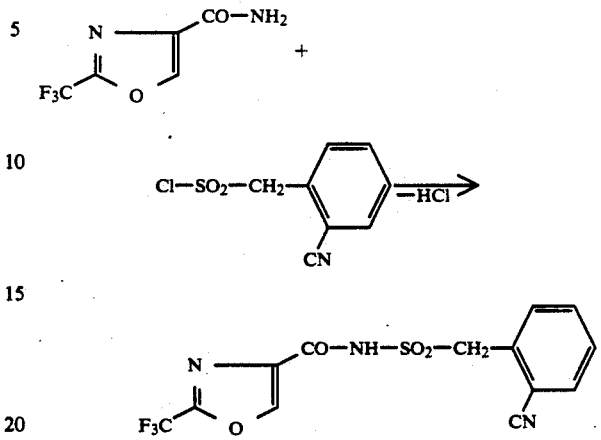

If, for example, methyl 5-methyl-isoxazole-3-carboxylate and 2,6-difluoro-benzene-sulphonamide are used as starting materials in process (b) according to the invention, the course of the reaction can be outlined by the following equation:

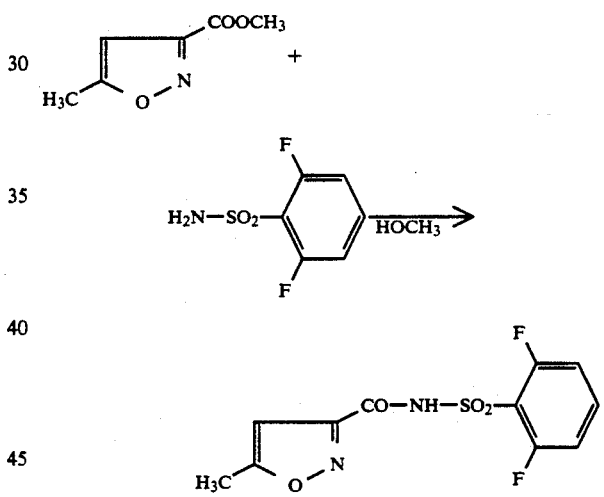

Formula (II) provides a general definition of the carboxamides to be used as starting materials in process (a) according to the invention for the preparation of compounds of the formula (I).

In formula (II), R¹ preferably or in particular has that meaning which has already been mentioned above as preferred or as particularly preferred for R¹ in connection with the description of the compounds of the formula (I) according to the invention.

Examples of the starting materials of the formula (II) which may be mentioned are: 5-methyl-, 5-ethyl-, 5-propyl-, 5-isopropyl-, 5-butyl-, 5-isobutyl-, 5-sec-butyl- and 5-tert-butyl-isoxazole-3-carboxamide, 2-methyl-, 2-ethyl-, 2-propyl-, 2-isopropyl-, 2-butyl-, 2-isobutyl-, 2-sec-butyl- and 2-tertbutyl-oxazole-4-carboxamide, 5-methyl-, 5-ethyl-, 5-propyl-, 5-isopropyl-, 5-butyl-, 5-isobutyl-, 5-secbutyl- and 5-tert-butyl-1,2,4-oxadiazole-3-carboxamide, 2-chloro-, 2-methyl-, 2-ethyl-, 2-propyl-, 2-isopropyl-, 2-butyl-, 2-isobutyl-, 2-sec-butyl-, 2-tert-butyl-, 2-trifluoromethyl-, 2-methoxy-, 2-ethoxy-, 2-propoxy- and 2-isopropoxythiazole-5-carboxamide, 2,4-dichloro-thiazole-5-carboxamide, 2-methyl-4-chloro-thiazole-5-carboxamide, 2-methoxy-4-chloro-thiazole-5-carboxamide, 4-methyl-, 4-ethyl-, 4-propyl-, 4-isopropyl-, 4-butyl-, 4-isobutyl-, 4-sec-butyl- and 4-tert-butyl-thiazole-2-carboxamide, 5-methyl-, 5-ethyl-, 5-propyl-, 5-isopropyl-5-butyl-, 5-isobutyl-, 5-sec-butyl- and 5-tert-butylthiazole-2-carboxamide.

The carboxamides of the formula (II) are known and/or can be prepared by methods known per se (compare RO-P 67,530 cited in Chem. Abstracts 95, 7258k; Helv. Chim. Acta 27 (1944), 1437–1438; Chem. Ber. 73 (1940), 1240–1252; J. Prakt. Chem. 314 (1972), 447–454).

Formula (III) provides a general definition of the sulphonylating agents further required as starting materials in process (a) according to the invention.

In formula (III), n, A and $R^2$ preferably or in particular have those meanings which have already been mentioned above as preferred or as particularly preferred for n, A and $R^2$ in connection with the description of the compounds of the formula (I) according to the invention and X preferably represents fluorine, chlorine or bromine, in particular chlorine.

Examples of the starting materials of the formula (III) which may be mentioned are: benzenesulphonyl chloride, 2-chloro-, 3-chloro-, 4-chloro-, 2,5-dichloro-, 2-fluoro-, 4-fluoro-, 2-bromo-, 4-bromo-, 2-cyano-, 2-nitro-, 4-nitro-, 2-methyl-, 4-methyl-, 2-chloromethyl-, 2-trifluoromethyl-, 2-methoxy-4-methoxy-, 2-methylthio, 2-trifluoromethylthio-, 2-difluoromethylthio-, 2-cyclopropyloxycarbonyl-, 2-phenoxy-, 2-difluoromethoxy-, 2-trifluoromethoxy-, 2-(2-chloroethoxy)-, 2-methylthiomethyl-, 2-dimethylaminosulphonyl-, 2-phenyl-, 2-methoxycarbonyl-, 2-ethoxycarbonyl-, 2-dimethylaminocarbonyl and 2-diethylaminocarbonyl-benzenesulphonyl chloride and also (2-chlorophenyl)-, (2-cyano-phenyl)-, (2-methoxycarbonyl-phenyl)- and (2-trifluoromethoxy-phenyl)-methanesulphonyl chloride, 2-chloro-6-methyl-benzenesulphonyl chloride and 2,6-dichloro-benzenesulphonyl chloride.

The sulphonylating agents of the formula (III) are known and/or can be prepared by processes which are known per se ()compare J. Org. Chem. 33 (1968), 2104; J. Org. Chem. 25 (1960), 1824; DE-AS (German Published Specification) 2,308,262; EP-OS (European Published Specification) 23,140, 23,141, 23,422, 35,893, 48,143, 51,466, 64,322, 70,041, 44,808 and 44,809; U.S. Pat. Nos. 2,929,820, 4,282,242; 4,348,220 and 4,372,778 and also Angew. Chem. 93 (1981), 151).

Process (a) according to the invention for the preparation of the new compounds of the formula (I) is preferably carried out using diluents. Suitable diluents in this case are virtually all the inert organic solvents. These preferably include aliphatic and aromatic, optionally halogenated hydrocarbons such as pentane, hexane, heptane, cyclhexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone and also dimethyl sulphoxide, tetramethylene sulphone and hexamethylphosphoric triamide and pyridine.

Acid acceptors which can be employed in process (a) according to the invention are all acid-binding agents which can customarily be used for reactions of this type. Those which are preferable are alkali metal hydroxides such as, for example, sodium hydroxide and potassium hydroxide, alkaline earth metal hydroxides such as, for example, sodium hydride and potassium hydride, alkaline earth metal hydrides such as, for example, calcium hydride, alkali metal carbonates and alkoxides such as sodium carbonate and potassium carbonate, sodium tert.-butoxide and potassium tert.-butoxide, and in addition aliphatic, aromatic or heterocyclic amines, for example triethylamine, trimethylamine, dimethylaniline, dimethylbenzylamine, pyridine, picoline, 1,5-diazabicyclo-[4.3.0]-non5-ene (DBN), 1,8-diazabicyclo-[5.4.0]-undec-7-ene (DBU) and 1,4-diazabicyclo-[2.2.2]-octane (DABCO).

To carry out process (a) according to the invention, the starting materials required in each case are in general employed in approximately equimolar amounts. However, it is also possible to use one of the two components employed in each case in a relatively large excess. The reaction are in general carried out in a suitable diluent in the presence of an acid acceptor, and the reaction mixture is stirred for several hours at the temperature required in each case. Working-up is in each case carried out in process (a) according to the invention by customary methods (compare the preparation examples).

Formula (IV) provides a general definition of the carboxylic acids required as starting materials in process (b) according to the invention.

In formula (IV), $R^1$ preferably or in particular has that meaning which has already been indicated as preferred or as particularly preferred for $R^1$ in connection with the description of the compounds of the formula (I) according to the invention.

Examples of the starting materials of the formula (IV) which may be mentioned are: 5-methyl-, 5-ethyl-, 5-propyl-, 5-isopropyl-, 5-butyl-, 5-isobutyl-, 5-sec-butyl- and 5-tert-butyl-isoxazole-3-carboxylic acid, 2-methyl-, 2-ethyl-, 2-propyl-, 2-isopropyl-, 2-butyl, 2-isobutyl-, 2-sec-butyl- and 2-tert-butyl-oxazole-4-carboxylic acid, 5-methyl-, 5-ethyl-, 5-propyl-, 5-isopropyl-, 5-butyl-, 5-isobutyl-, 5-sec-butyl- and 5-tert-butyl-1,2,4-oxadiazole-3-carboxylic acid, 2-chloro, 2-methyl-, 2-ethyl-, 2-propyl-, 2-isopropyl-, 2-butyl-, 2-isobutyl-, 2-sec-butyl, 2-tertbutyl-, 2-trifluoromethyl-, 2-methoxy-, 2-ethoxy-, 2-propoxy- and 2-isopropyl-thiazole-5-carboxylic acid, 2,4-dichloro-thiazole-5-carboxylic acid, 2-methyl-4-chloro-thiazole-5-carboxylic acid, 2-methoxy-4-chloro-thiazole-5-carboxylic acid, 4-methyl-, 4-ethyl-, 4-propyl, 4-isopropyl-, 4-butyl-, 4-isobutyl-, 4-sec-butyl- and 4-tert-butyl-thiazole-2-carboxylic acid, 5-methyl-, 5-ethyl-, 5-propyl-, 5-isopropyl-, 5-butyl-, 5-isobutyl-, 5-sec-butyl- and 5-tert-butyl-thiazole-2-carboxylic acid.

The carboxylic acids of the formula (IV) are known and/or can be prepared by known processes (compare GB-P 1,245,517; DE-OS (German Published Specification) 2,940,189; DE-OS (German Published Specification) 3,013,908; Helv. Chim. Acta 27 (1944), 1437–1438; Chem. Ber. 73 (1940), 1240–1252; J. Chem. Soc. 1946, 87–91; loc. cit. 1947, 96–102; Helv. Chim. Acta 29 (1946), 1957–1959; J. Prakt. Chem. 314 (1972), 447–454; Chem. Ber. 94 (1961), 757–761).

Instead of the carboxylic acids of the formula (IV), the carbonyl chlorides derived therefrom or alkyl esters derived therefrom (preferably methyl esters or ethyl esters), aralkyl esters (preferably benzyl esters) or aryl esters (preferably phenyl esters, optionally substituted in the phenyl group by cyano, nitro, chlorine, fluorine, bromine and/or methyl) may be employed as starting materials ("reactive derivatives") in process (b) according to the invention.

The carbonyl chlorides are obtained from the corresponding carboxylic acids by customary methods, for example by reaction with customary "chlorinating agents" such as, for example, phosgene, oxalyl chloride or thionyl chloride, if appropriate in the presence of reaction auxiliaries, such as, for example, pyridine, and if appropriate in the presence of diluents, such as, for example, chloroform or tetrachloromethane, at temperatures between 0° C. and 100° C.

The corresponding esters of the formula (IV) can be obtained from the appropriate carbonyl chlorides and suitable alcohols or phenols by customary methods, in general by reaction in the presence of an acid acceptor, such as, for example, triethylamine or pyridine, and in the presence of a diluent, such as, for example, acetonitrile, at temperatures between 0° C. and 100° C.

However, the esters mentioned can also be obtained directly from the carboxylic acids of the formula (IV) in the presence of condensation auxiliaries, such as, for example, dicyclohexylcarbodiimide, if appropriate in the presence of reaction auxiliaries, such as, for example, 4-dimethylamino-pyridine, and if appropriate in the presence of diluents, such as, for example, methylene chloride or chloroform, at temperatures between 0° C. and 100° C.

Formula (V) provides a general definition of the aminosulphonyl compounds further required as starting materials in process (b) according to the invention.

In formula (V), n, A and $R^2$ preferably or in particular have those meanings which have preferred for n, A and $R^2$ in connection with the description of the compounds of the formula (I) according to the invention.

Examples of the starting materials of the formula (V) which may be mentioned are: benzenesulphonamide, 2-chloro-, 3-chloro-, 4-chloro-, 2,5-dichloro-, 2-fluoro-, 4-fluoro-, 2-bromo-, 4-bromo-, 2-cyano-, 2-nitro-, 4-nitro-, 2-methyl-, 4-methyl-, 2-chloromethyl-, 2-trifluoromethyl-, 2-methoxy-, 4-methoxy-, 2-methylthio-, 2-trifluoromethylthio-, 2-difluoromethylthio-, 2-cyclopropyloxycarbonyl-, 2-phenoxy-, 2-difluoromethoxy-, 2-trifluoromethoxy-, 2-(2-chloroethoxy), 2-methylthiomethyl-, 2-dimethylaminosulphonyl-, 2-phenyl-, 2-methoxycarbonyl-, 2-ethoxycarbonyl-, 2-dimethylaminocarbonyl- and 2-diethylaminocarbonylbenzenesulphonamide and also (2-chloro-phenyl)-, (2-cyano-phenyl)-, (2-methoxycarbonyl-phenyl)- and (2-trifluoromethoxy-phenyl)-methanesulphonamide, 2-chloro-6-methyl-benzenesulphonyl chloride and 2,6-dichlorobenzenesulphonamide.

The aminosulphonyl compounds of the formula (V) are known and/or can be prepared by process which are known per se (compare J. Org. Chem. 33 (1968), 2104; J. Org. Chem. 25 (1960), 1824; DE-AS (German Published Specification) 2,308,262; EP-A 23,140, 23,141, 23,422, 35,893, 48,143, 51,466, 64,322, 70,041, 44,808 and 44,809; U.S. Pat. Nos. 2,929,820, 4,282,242; 4,348,220 and 4,372,778 and also Angew. Chem. 93 (1981), 151).

Instead of the aminosulphonyl compounds of the formula (V), the sulphonyl isocyanates derived therefrom ("reactive derivatives") may be employed as starting materials in process (b) according to the in invention. These compounds are known and/or can be prepared by methods which are known per se (compare J. Org. Chem. 31 (1966), 2658–2661; EP-A 7687; EP-A 46,626; EP-A 21,641; EP-A 23,140; EP-A 23,141; EP-A 70,041; EP-A 23,422, EP-A 64,322; EP-A 34,431; EP-A 35,893, EP-A 51,466, EP-A 44,808; EP-A 173,312, DE-OS (German Published Specification) 3,132,944; EP-A 87,780; EP-A 271,780).

Process (b) according to the invention for the preparation of the new compounds of the formula (I) is preferably carried out using diluents. Possible diluents in this case are preferably the same diluents which are indicated above for process (a) according to the invention.

Process (b) according to the invention is optionally carried out in the presence of a reaction auxiliary. Suitable reaction auxiliaries in this case are compounds with which carboxylic acids are converted into reactive intermediates which are then reacted in situ with nucleophilic compounds, such as, for example, the sulphonamides of the formula (V) to give corresponding carboxylic acid derivatives. Examples of reaction auxiliaries of this type which may be mentioned are carbonyldiimidazole and 2-chloro-1-methyl-pyridinium iodide.

For the reaction of the carbonyl chlorides and esters according to formula (IV) with aminosulphonyl compounds of the formula (V), acid acceptors such as have been indicated above for process (a) according to the invention are also suitable as reaction auxiliaries.

The reaction temperatures in process (b) according to the invention can be varied within a substantial range. In general, the reaction is carried out at temperatures between 0° C. and 150° C., preferably at temperatures between 10° C. and 100° C.

Process (b) according to the invention is in general carried out under normal pressure. However, it is also possible to work at elevated or reduced pressure.

To carry out process (b) according to the invention, the starting materials required in each case are in general employed in approximately equimolar amounts. However it is also possible to use one of the two components employed in each case in a relatively large excess. The reactions are in general carried out in the presence of a suitable diluent and if appropriate in the presence of a reaction auxiliary, and the reaction mixture is stirred for several hours at the temperature required in each case. Working-up is carried out by customary methods.

Salts may optionally be prepared from the compounds of the general formula (I) according to the invention. Such salts are obtained in a simple manner by customary salt formation methods, for example by dissolving or dispersing a compound of the formula (I) in a suitable solvent, such as, for example, water, methanol, ethanol, methylene chloride or acetone, and adding a suitable acid or base. The salts can then be isolated—if appropriate after stirring for a relatively long time —by concentrating or filtering off with suction.

The active compounds according to the invention can be used as defoliants, desiccants, agents for destroying broad-leaved plants and, especially, as weedkillers. By weeks, int he broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Conchus, Solanum, Rorippa, Rotala, Lindernia, Lamiu, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Elusine, Brachiaria, Lolium, Bromus, Avena, Cyperus, Sorghum, Agropyron, Gynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example aforestations, decorative tree plantings, orchards, vineyards, citrus groves, nut orchards, banana plantations, coffee plantations, tea plantations, rubber plantation, oil palm plantations, cocoa plantations, soft fruit plantings and hopfields, on lawns, turf and pastureland and for the selective combating of weeds in annual cultures.

The compounds of the formula (I) are in particular suitable for the selective combating of dicotyledon weeds in monocotyledon cultures, such as, for example, in corn and wheat, both in the pre-emergence and in the post-emergence process.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol and glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural minerals such as calcite, marble, pumice, sepiolite and dolomite, as well as synthetic granules of inorganic and organic meals, and granules or organic material such as sawdust, coconut shells, corn cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) OR N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans; in addition also 2,4-dichlorophebnoxyacetic acid (2,4-D); 4-(2,4-dichlorophenoxy)-butyric acid (2,4-DB); 2,4-dichlorophenoxypropionic acid (2,4-DP); 2-chloro-2',6'-diethyl-N-methoxymethyl-acetanilide (ALACHLOR); 2-chloro-4-ethylamino-6-isopropylamino-1,3,5-triazine (ATRAZINE); 3-isopropyl-2,1,3-benzothiadiazin-4-one-2,2-dioxide (BENTAZONE); METHYL 5-(2,4-dichlorophenoxy)-2-nitrobenzoate (BIFENOX); 3,5-dibromo-4-hydroxy-benzonitrile (BROMOXYNIL); 2-chloro-N-{[(4-methoxy-6-methyl-1,3,5-traizin-2-yl)-amino]-carbonyl}benzenesulphonamide (CHLORSULFURON); N,N-dimethyl-N'-(3-chloro-4-methylphenyl)-urea (CHLOROTOLURON); 2-chloro-4-ethylamino-6-(3-cyanopropylamino);-1,3,5-triazine (CYANAZINE); 2-[4-(2,4-dichlorophenoxy)-phenoxy]-propionic acid, its methyl ester or its ethyl ester (DICLOFOP); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); [(4-amino-3,5-dichloro-6-fluoro-2-pyridinyl)-oxy]-acetic acid or its 1-methylheptyl ester (FLUROXYPYR); N-phosphonomethylglycine (GLYPHOSATE); methyl-2-[4,5-dihydro-4-methyl-4-(1-methylethyl)-5-oxo-1H-imidazol-2-yl]-4(5)-methylbenzoate (IMAZAMETHABENZ); 3,5-diiodo-4-hydroxybenzonitrile (IOXYNIL); N,N-dimethyl-N'-(4-isopropylphenyl)urea (ISOPROTURON); (2-methyl-4-chlorophenoxy)-acetic acid (MCPA); (4-chloro-2-methylphenoxy)-propionic acid (MCPP); 2-ethyl-6-methyl-N-(1-methyl-2-methoxyethyl)chloroacetanilide (METOLACHLOR); 2-{[[((4-methoxy-6-methyl-1,3,5-triazin-2-yl)-amino)-carbonyl]-amino-sulphonyl}-benzoic acid or its methyl ester (METSULFURON); N-(1-ethylpropyl)-3,4-dimethyl-2,6-dinitroaniline (PENDIMETHALIN); O-(6-chloro-3-phenyl-pyridazin-4-yl) S-octyl thiocarbonate (PYRIDATE); 4-ethylamino-2-t-butylamino-6-methylthio-s-triazine (TERBUTRYNE); methyl 3-[[[[(4-methoxy-6-methyl-1,3,5-triazin-2-yl)-amino]carbonyl]-amino]-sulphonyl]-thiophene-2-carboxylate (THIAMETURON); and S-(2,3,3-trichloroallyl) N,N-diisopropylthiocarbamate (TRIALLATE). Surprisingly, some mixtures also shown a synergistic action.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES

EXAMPLE 1

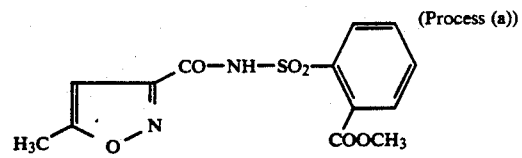

(Process (a))

2.52 g (0.02 mol) of 5-methyl-isoxazole-3-carboxamide are dissolved in 50 ml of 1,4-dioxane and after adding 3.4 g (0.06 mol) of powdered potassium hydroxide the mixture is stirred at 80° C. for 30 minutes. The mixture is cooled, 5.7 g (0.022 mol) of methyl 2-chlorosulphonylbenzoate are added at room temperature for 20 hours. The solvent is then distilled off in vacuo, the residue is taken up in water and the solution is filtered. The product precipitates from the filtrate on acidifying with hydrochloric acid, and is collected on a suction filter and dried on clay.

1.8 g (27% of theory) of N-(2-methoxycarbonyl-phenylsulphonyl)-5-methyl-isoxazole-3-carboxamide of melting point 101° C. are obtained.

EXAMPLE 2

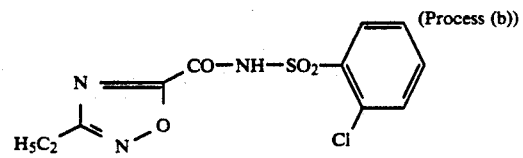

(Process (b))

3.8 g (0.02 mol) of 2-chlorobenzenesulphonamide are converted into the sodium salt by dissolving it in 100 ml of methanol, adding 1.1 g (0.02 mol) of sodium methoxide, subsequently stirring for 10 minutes and evaporating to dryness. The sodium salt is heated under reflux in 100 ml of acetonitrile with 3.4 g (0.02 mol) of ethyl 3-ethyl-1,2,4-oxadiazole-5-carboxylate for 12 hours. The residue remaining after distilling off the solvent is stirred with 100 ml of 10% strength potassium carbonate solution, filtered off with suction, washed with 1N hydrochloric acid and water and dried in a desiccator.

4.6 g (73% of theory) of N-(2-(chlorophenylsulphonyl)-3-ethyl-1,2,4-oxadiazole-5-carboxamide of melting point 142° C. are obtained.

The compounds of the formula (I) shown in Table 2 below can also be prepared, for example, analogously to Examples 1 or 2 and corresponding to the general description of the preparation process according to the invention.

$$R^1-CO-NH-SO_2-(A)_n-R^2 \qquad (I)$$

TABLE 2

Examples of the compounds of the formula (I)

| Ex. No. | $R^1$ | A | n | $R^2$ | Melting point (°C.) |
|---|---|---|---|---|---|
| 3 | 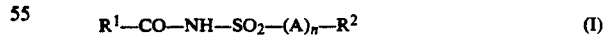 | — | 0 | (phenyl with OCF$_3$) | 110 |

TABLE 2-continued

Examples of the compounds of the formula (I)

| Ex. No. | R¹ | A | n | R² | Melting point (°C.) |
|---|---|---|---|---|---|
| 4 | (1,2,4-oxadiazole: H₃C-C(=N-O-N=)-CH₃) | — | 0 | 2-CF₃-phenyl | |
| 5 | (1,2,4-oxadiazole: H₃C-C(=N-O-N=)-CH₃) | — | 0 | 2-Cl, 6-CH₃-phenyl | |
| 6 | (isoxazole: H₃C-C=CH-C(-O-N=)-) | — | 0 | 2-Cl-phenyl | 185 |
| 7 | (isoxazole) | — | 0 | 2-OCH₃-phenyl | 167 |
| 8 | (isoxazole) | — | 0 | 2-COOC₂H₅-phenyl | 145 |
| 9 | (isoxazole) | — | 0 | 2-Cl, 6-CH₃-phenyl | |
| 10 | (isoxazole) | CH₂ | 1 | 2-COOCH₃-phenyl | 120 |
| 11 | (isoxazole) | CH₂ | 1 | 2-OCF₃-phenyl | 115 |
| 12 | H₃CO-C(=N-)-S-C(Cl)=C(CH₃)- | — | 0 | 2-OCF₃-phenyl | |

TABLE 2-continued

Examples of the compounds of the formula (I)

| Ex. No. | R¹ | A | n | R² | Melting point (°C.) |
|---|---|---|---|---|---|
| 13 | Cl, CH₃ substituted thiazole with H₃CO-C(=N)-S- | — | 0 | phenyl with o-CF₃ | |
| 14 | 1,2,4-oxadiazole with i-H₇C₃ and CH₃ | — | 0 | phenyl with o-OCF₃ | 112 |
| 15 | 1,2,4-oxadiazole with H₅C₂ and CH₃ | — | 0 | phenyl with o-OCF₃ | 107 |
| 16 | 1,2,4-oxadiazole with H₅C₂ and CH₃ | — | 0 | phenyl with o-OCHF₂ | 80 |
| 17 | 1,2,4-oxadiazole with H₅C₆ and CH₃ | — | 0 | phenyl with o-OCF₃ | 196 |
| 18 | 1,2,4-oxadiazole with H₅C₆ and CH₃ | — | 0 | phenyl with o-OCHF₂ | 148 |
| 19 | 1,2,4-oxadiazole with H₅C₆ and CH₃ | — | 0 | phenyl with o-Cl | 175 |
| 20 | 1,2,4-oxadiazole with H₅C₆ and CH₃ | — | 0 | phenyl with o-SO₂N(CH₃)₂ | 197 |
| 21 | 1,2,4-oxadiazole with H₅C₆ and CH₃ | — | 0 | phenyl with m-SO₂N(CH₃)₂ | 147 |
| 22 | thiazole with H₃C and CH₃ | — | 0 | phenyl with o-CF₃ | |

TABLE 2-continued

Examples of the compounds of the formula (I)

| Ex. No. | R¹ | A | n | R² | Melting point (°C.) |
|---|---|---|---|---|---|
| 23 | H₃C-C(=N-O-N=C(CH₃))- (oxadiazole ring with H₃C and CH₃ substituents) | — | 0 | 2-OCF₃-phenyl | |
| 24 | H₃C-C(=CH-O-C(CH₃))= (isoxazole-type with H₃C and CH₃) | — | 0 | 2-F₃CO-phenyl | 147 |
| 25 | H₅C₂-C(=N-O-N=C(CH₃))- | — | 0 | 2-SO₂N(CH₃)₂-phenyl | 147 |
| 26 | H₅C₆-C(=N-O-N=C(CH₃))- | — | 0 | 2-SO₂N(CH₃)₂-phenyl | 197 |
| 27 | H₅C₂-C(=N-O-N=C(CH₃))- | CH₂ | 1 | 2-OCF₃-phenyl | 118 |

EXAMPLE 28

The sodium salt of the compound shown as Example 9 can be prepared, for example, as follows:

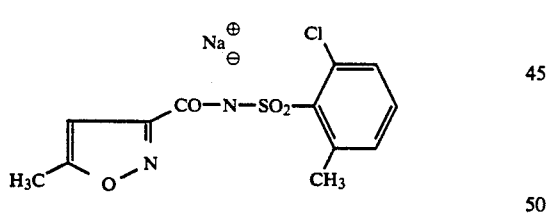

3.0 g (9.5 mmol) of N-(2-chloro-6-methyl-phenylsulphonyl)-5-methyl-isoxazole-3-carboxamide are dissolved in 50 ml of methylene chloride; 0.4 g (9.5 mmol) of sodium hydroxide (powder) is then added to this solution and the mixture is stirred at 20° C. for 12 hours. The product which is obtained in crystalline form is isolated by filtering off with suction.

2.5 g (77% of theory) of sodium N-(2-chloro-6-methylphenylsulphonyl)-5-methyl-isoxazole-3-carboxamide of melting point 270° C. (decomposition) are obtained.

Examples of other salts which can be obtained analogously are shown below.

EXAMPLE 29

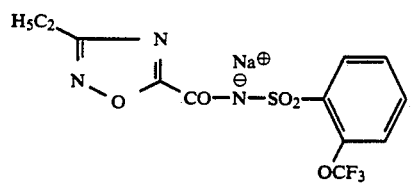

EXAMPLE 30

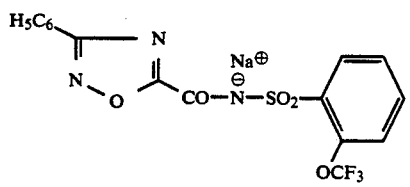

Other compounds of the formula (I) which can be prepared analogously to Examples 1 and 2 are:

TABLE 2 Continuation

| Example No. | R¹ | A | n | R² | (position-) R³ | Melting point (°C.) |
|---|---|---|---|---|---|---|

-continued
| | | | | | |
|---|---|---|---|---|---|
| 31 | 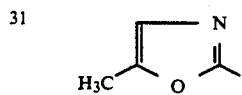 | — | 0 | 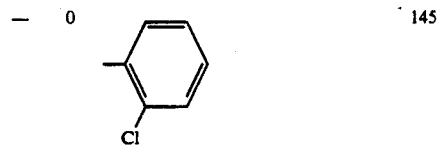 | 145 |
| 32 | 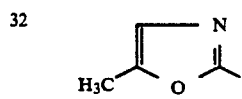 | — | 0 | 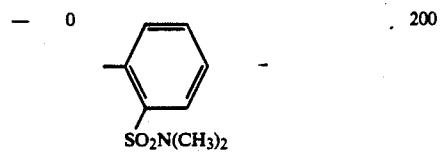 | 200 |
| 33 | 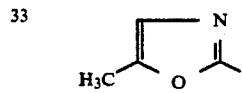 | CH$_2$ | 1 | 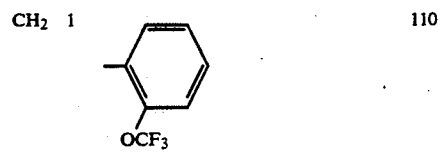 | 110 |
| 34 | 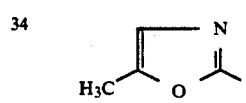 | — | 0 | 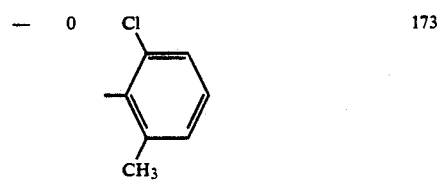 | 173 |
| 35 | 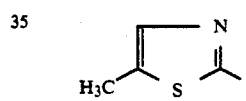 | CH$_2$ | 1 | 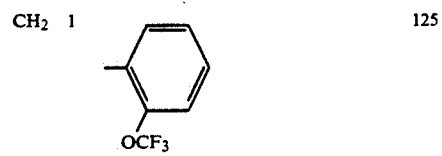 | 125 |
| 36 | 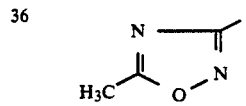 | — | 0 | 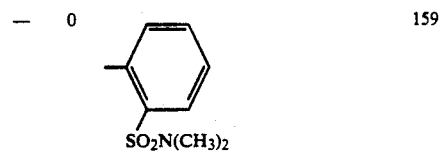 | 159 |
| 37 | 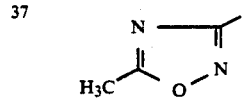 | — | 0 | 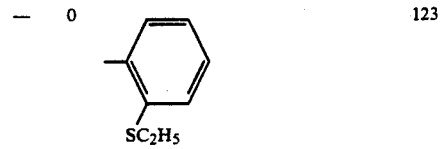 | 123 |
| 38 | 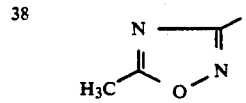 | — | 0 | 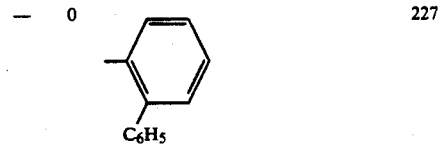 | 227 |
| 39 | 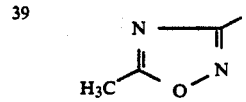 | — | 0 | 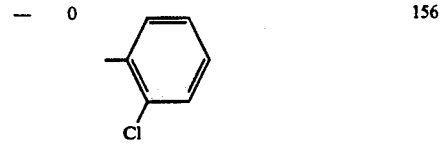 | 156 |
| 40 | 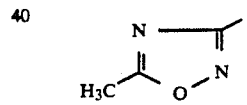 | — | 0 | 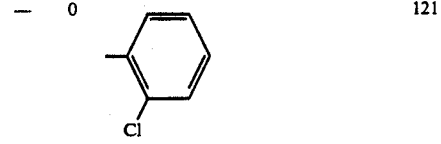 | 121 |

| | | | | -continued | | |
|---|---|---|---|---|---|---|
| 41 | 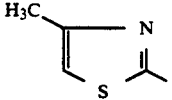 | — | 0 | 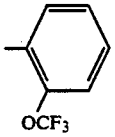 | | 298 |
| 42 | 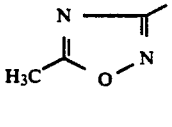 | — | 0 | 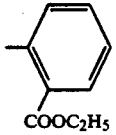 | | 129 |
| 43 | 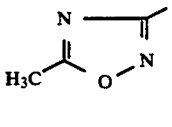 | — | 0 | 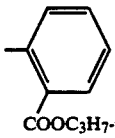 | | 78 |
| 44 | 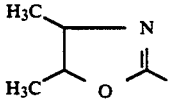 | — | 0 | CO$_2$CH$_3$ | — | 114 |
| 45 |  | — | 0 | COOCH$_3$ | — | 107 |
| 46 | 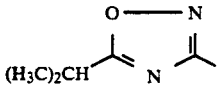 | — | 0 | CO$_2$CH$_3$ | — | Oil |
| | (n-C$_4$H$_9$)$_3$NH$^\oplus$ | | | | | Salt/Oil |
| | Na$^\oplus$ | | | | | Salt/Oil |
| | (C$_2$H$_5$)$_3$NH$^\oplus$ | | | | | Salt/Oil |
| | (HOCH$_2$CH$_2$)$_3$NH$^\oplus$ | | | | | Salt/Oil |
| 47 |  | — | 0 | CO$_2$CH(CH$_3$)$_2$ | — | 108 |
| 48 | 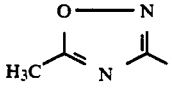 | CH$_2$ | 1 | COOCH$_3$ | — | 132 |
| 49 |  | CH$_2$ | 1 | OCF$_3$ | — | 214 |
| 50 | 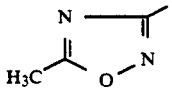 | — | 0 | COOC$_2$H$_5$ | — | 150 |
| 51 | 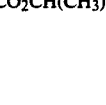 | — | 0 | COOC$_3$H$_7$ | — | 144 |
| 52 | 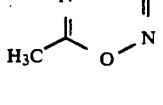 | — | 0 | COOCH$_3$ | — | 146 |

| | | | | | | |
|---|---|---|---|---|---|---|
| 53 | 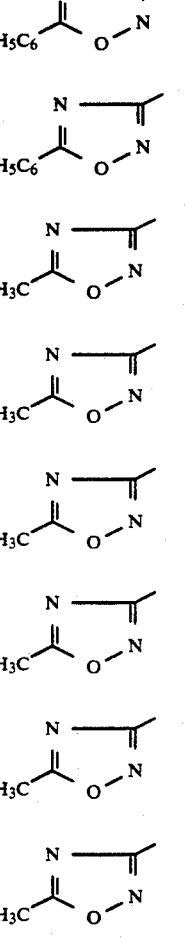(CH₃)₂CH | — | 0 | SOC₂H₅ | — | 170 |
| 54 | 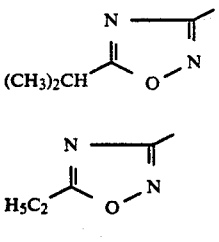H₅C₆ | — | 0 | SOC₂H₅ | — | 184 |
| 55 | 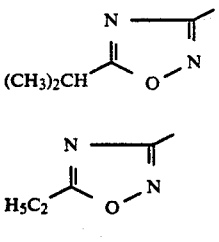H₅C₆ | — | 0 | SO₂C₂H₅ | — | 208 |
| 56 | 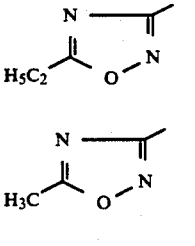H₃C | O | 1 | CH₃ | — | 178 |
| 57 | 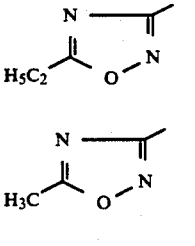H₃C | — | 0 | SCH₃ | — | 130 |
| 58 | 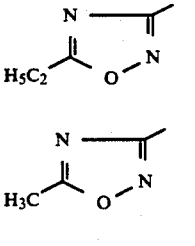H₃C | — | 0 | SC₃H₇ | — | 121 |
| 59 | 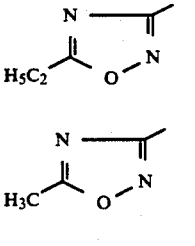H₃C | — | 0 | SOC₂H₅ | — | 166 |
| 60 | 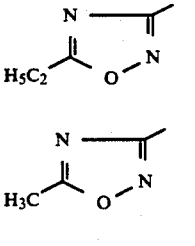H₃C | — | 0 | SO₂C₂H₅ | — | 165 |
| 61 | 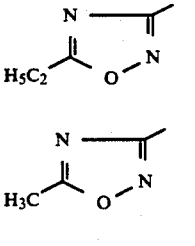H₃C | — | 0 | SOC₃H₇ | — | 162 |
| 62 | 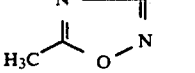(CH₃)₂CH | — | 0 | COOC₂H₅ | — | 84 |
| 63 | H₅C₂ | — | 0 | COOCH₃ | — | 121 |
| 64 | H₅C₂ | — | 0 | COOC₂H₅ | — | 84 |
| 65 | H₃C | — | 0 | COOCH₂CH₂Cl | — | 93 |
| 66 | H₃C | — | 0 | COOCH₂CH₂OCH₃ | — | 129 |

-continued

| | | | | | | |
|---|---|---|---|---|---|---|
| 67 | ethyl-substituted 1,2,4-oxadiazole with methyl | — | 0 | COOCH$_3$ | — | 118 |
| 68 | 5-methylisoxazol-3-yl with methyl | — | 0 | COOCH$_3$ | — | 122 |
| 69 | 5-methylisoxazol-3-yl with methyl | — | 0 | COOC$_2$H$_5$ | — | 116 |
| 70 | 3-methyl-1,2,4-oxadiazol-5-yl with methyl | — | 0 | OCH$_3$ | — | 161 |
| 71 | 3-methyl-1,2,4-oxadiazol-5-yl with methyl | — | 0 | OC$_2$H$_5$ | — | 165 |
| 72 | 4-methylthiazol-2-yl with methyl | — | 0 | COOCH$_3$ | — | 121 |
| 73 | 3-methyl-1,2,4-oxadiazol-5-yl with methyl | — | 0 | COOH | — | 178 |
| 74 | 4,5-dimethyloxazol-2-yl with methyl | — | 0 | COOC$_2$H$_5$ | — | 108 |
| 75 | 4,5-dimethyloxazol-2-yl with methyl | — | 0 | OCH$_3$ | — | 174 |
| 76 | 4,5-dimethyloxazol-2-yl with methyl | — | 0 | SC$_2$H$_5$ | — | 124 |
| 77 | 4,5-dimethyloxazol-2-yl with methyl | — | 0 | C$_6$H$_5$ | — | 140 |
| 78 | 4,5-dimethyloxazol-2-yl with methyl | — | 0 | OCF$_3$ | — | 110 |
| 79 | 4,5-dimethyloxazol-2-yl with methyl | — | 0 | F | — | 104 |
| 80 | 4,5-dimethyloxazol-2-yl with methyl | — | 0 | Cl | (3-)Cl | 125 |

-continued

| | | | | | | |
|---|---|---|---|---|---|---|
| 81 | H3C-, H3C- isoxazole | — | 0 | Cl | (5-)CH3 | 191 |
| 82 | H3C-, H3C- isoxazole | — | 0 | SC3H7 | — | 121 |
| 83 | H3C-, H3C- isoxazole | — | 0 | COOCH2CH2Cl | — | 115 |
| 84 | H3C-, H3C- isoxazole | CH2 | 1 | COOCH3 | — | 113 |
| 85 | (CH3)2N-thiazole | — | 0 | COOCH3 | — | — |
| 86 | H-oxadiazole | — | 0 | COOCH3 | — | — |
| 87 | H-oxadiazole | — | 0 | COOC2H5 | — | — |
| 88 | H-oxadiazole | — | 0 | OCH3 | — | — |
| 89 | H-oxadiazole | — | 0 | OC2H5 | — | — |
| 90 | H-oxadiazole | — | 0 | SC2H5 | — | — |
| 91 | H-oxadiazole | — | 0 | C6H5 | — | — |
| 92 | F3C-oxadiazole | — | 0 | COOCH3 | — | — |
| 93 | (CH3)2N-oxadiazole | — | 0 | COOC2H5 | — | — |
| 94 | Cl3C-oxadiazole | — | 0 | OC2H5 | — | — |

| No. | Structure | | | | |
|---|---|---|---|---|---|
| 95 | 3-methyl-5-bromo-1,2,4-oxadiazole | — | 0 | COOCH$_3$ | — |
| 96 | 3-methyl-5-methoxy-1,2,4-oxadiazole | — | 0 | COOC$_2$H$_5$ | — |
| 97 | 2,5-dimethyl-1,3,4-oxadiazole | — | 0 | COOCH$_3$ | — |
| 98 | 2,5-dimethyl-1,3,4-oxadiazole | — | 0 | COOC$_2$H$_5$ | — |
| 99 | 2,5-dimethyl-1,3,4-oxadiazole | — | 0 | OC$_2$H$_5$ | — |
| 100 | 2,5-dimethyl-1,3,4-oxadiazole | — | 0 | Cl | — | 179° C. (Zers.) |
| 101 | 2-phenyl-5-methyl-1,3,4-oxadiazole | — | 0 | Cl | — | 195° C. (Zers.) |
| 102 | 2,5-dimethyl-1,3,4-thiadiazole | — | 0 | COOCH$_3$ | — |
| 103 | 2,5-dimethyl-1,3,4-thiadiazole | — | 0 | COOC$_2$H$_5$ | — |
| 104 | 2-methoxy-5-methyl-1,3,4-thiadiazole | — | 0 | COOCH$_3$ | — |
| 105 | 2-methylthio-5-methyl-1,3,4-thiadiazole | — | 0 | OC$_2$H$_5$ | — |
| 106 | 2-methylsulfonyl-5-methyl-1,3,4-thiadiazole | — | 0 | SC$_2$H$_5$ | — |
| 107 | 3,5-dimethyl-1,2,4-oxadiazole | — | 0 | Cl | (6)-Cl |
| 108 | 3,5-dimethyl-1,2,4-oxadiazole | — | 0 | CO$_2$CH$_3$ | (5)-Cl |
| 109 | 3,5-dimethyl-1,2,4-oxadiazole | — | 0 | O—C$_3$H$_{7-n}$ | — |

-continued

| No. | Structure | | | R | Position |
|---|---|---|---|---|---|
| 110 | oxadiazole with H3C-C(=N-)-O-N=C(CH3)- | — | 0 | O—C3H7-i | — |
| 111 | oxadiazole with H5C2-C(=N-)-O-N=C(CH3)- | — | 0 | Cl | (6)-Cl |
| 112 | oxadiazole with H5C2-C(=N-)-O-N=C(CH3)- | — | 0 | CO2CH3 | (5)-Cl |
| 113 | oxadiazole with H5C2-C(=N-)-O-N=C(CH3)- | — | 0 | O—C3H7-n | — |
| 114 | oxadiazole with H5C2-C(=N-)-O-N=C(CH3)- | — | 0 | O—C3H7-i | — |
| 115 | oxadiazole with n-H7C3-C(=N-)-O-N=C(CH3)- | CH2 | 1 | CO2CH3 | — |
| 116 | oxadiazole with i-H7C3-C(=N-)-O-N=C(CH3)- | — | 0 | CO2CH3 | — |
| 117 | oxadiazole with Cl-CH2-C(=N-)-O-N=C(CH3)- | — | 0 | CO2CH3 | — |
| 118 | oxadiazole with Cl-CH2-C(=N-)-O-N=C(CH3)- | — | 0 | CO2C2H5 | — |
| 119 | oxadiazole with Cl-CH2-C(=N-)-O-N=C(CH3)- | — | 0 | Cl | — |
| 120 | oxadiazole with Cl-CH2-C(=N-)-O-N=C(CH3)- | — | 0 | Br | — |
| 121 | oxadiazole with Cl-CH2-C(=N-)-O-N=C(CH3)- | — | 0 | F | — |
| 122 | oxadiazole with Cl-CH2-C(=N-)-O-N=C(CH3)- | — | 0 | C6H5 | — |
| 123 | oxadiazole with Cl-CH2-C(=N-)-O-N=C(CH3)- | — | 0 | OCH3 | — |
| 124 | oxadiazole with Cl-CH2-C(=N-)-O-N=C(CH3)- | — | 0 | OC2H5 | — |

-continued
| | | | | | |
|---|---|---|---|---|---|
| 125 | 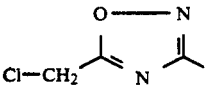 | — | 0 | OC$_3$H$_7$ | — |
| 126 | 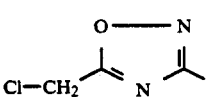 | — | 0 | SCH$_3$ | — |
| 127 | 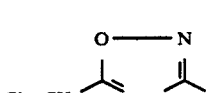 | — | 0 | SC$_2$H$_5$ | — |
| 128 | 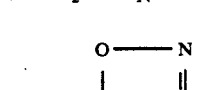 | — | 0 | CO$_2$CH$_3$ | (5)-Cl |
| 129 | 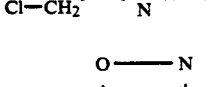 | — | 0 | CO$_2$CH$_2$CH$_2$Cl | — |
| 130 | 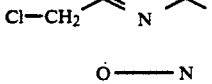 | — | 0 | Cl | (6)-Cl |
| 131 | 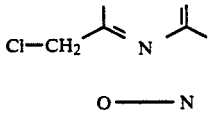 | — | 0 | Cl | (6)-CH$_3$ |
| 132 | 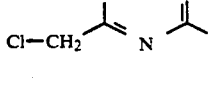 | — | 0 | OCF$_3$ | — |
| 133 | 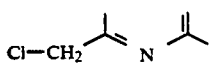 | — | 0 | OCHF$_2$ | — |
| 134 | 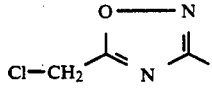 | CH$_2$ | 1 | OCF$_3$ | — |
| 135 | 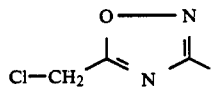 | O | 1 | CH$_3$ | — |
| 136 | 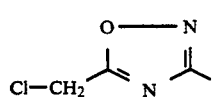 | — | 0 | CH$_3$ | — |
| 137 | 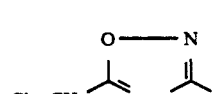 | — | 0 | CO$_2$CH$_3$ | — |
| 138 | 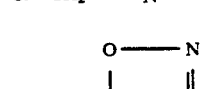 | — | 0 | CO$_2$CH$_3$ | (5)-Cl |
| 139 | 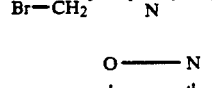 | — | 0 | CO$_2$C$_2$H$_5$ | — |

-continued

| # | Structure | | n | R | R' |
|---|---|---|---|---|---|
| 140 | Br—CH₂–C(=N—O—)–N=C(CH₃) | — | 0 | Cl | — |
| 141 | Br—CH₂–C(=N—O—)–N=C(CH₃) | — | 0 | OCH₃ | — |
| 142 | Br—CH₂–C(=N—O—)–N=C(CH₃) | — | 0 | OC₂H₅ | — |
| 143 | Br—CH₂–C(=N—O—)–N=C(CH₃) | — | 0 | OC₃H₇ | — |
| 144 | Br—CH₂–C(=N—O—)–N=C(CH₃) | — | 0 | C₆H₅ | — |
| 145 | Br—CH₂–C(=N—O—)–N=C(CH₃) | — | 0 | Cl | (6)-Cl |
| 146 | Br—CH₂–C(=N—O—)–N=C(CH₃) | — | 0 | Cl | (6)-CH₃ |
| 147 | Br—CH₂–C(=N—O—)–N=C(CH₃) | — | 0 | SCH₃ | — |
| 148 | Br—CH₂–C(=N—O—)–N=C(CH₃) | — | 0 | OCF₃ | — |
| 149 | Br—CH₂–C(=N—O—)–N=C(CH₃) | — | 0 | SC₂H₅ | — |
| 150 | Br—CH₂–C(=N—O—)–N=C(CH₃) | — | 0 | OCHF₂ | — |
| 151 | F₃C–C(=N—O—)–N=C(CH₃) | CH₂ | 1 | CO₂CH₃ | — |
| 152 | F₃C–C(=N—O—)–N=C(CH₃) | — | 0 | CO₂C₆H₅ | — |
| 153 | F₃C–C(=N—O—)–N=C(CH₃) | — | 0 | C₆H₅ | — |
| 154 | F₃C–C(=N—O—)–N=C(CH₃) | — | 0 | Cl | — |

-continued
| | | | | | |
|---|---|---|---|---|---|
| 155 | 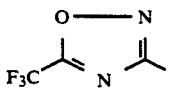 | — | 0 | Cl | (6)-Cl |
| 156 | 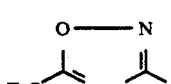 | — | 0 | OCH$_3$ | — |
| 157 | 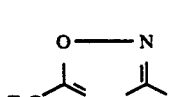 | — | 0 | OC$_2$H$_5$ | — |
| 158 | 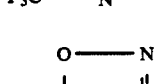 | — | 0 | SO$_2$N(CH$_3$)$_2$ | — |
| 159 | 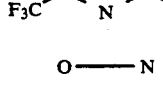 | — | 0 | SCH$_3$ | — |
| 160 | 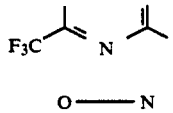 | — | 0 | SC$_2$H$_5$ | — |
| 161 | 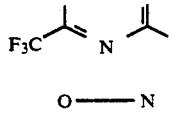 | — | 0 | SOC$_2$H$_5$ | — |
| 162 | 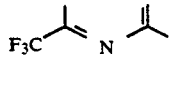 | — | 0 | SO$_2$C$_3$H$_{7-n}$ | — |
| 163 | 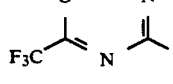 | — | 0 | CH$_3$ | — |
| 164 | 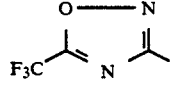 | — | 0 | CO$_2$CH$_3$ | — |
| 165 | 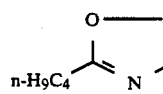 | — | 0 | OCF$_3$ | — |
| 166 | 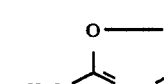 | — | 0 | CO$_2$CH$_3$ | — |
| 167 | 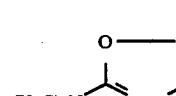 | — | 0 | CO$_2$CH$_3$ | — |
| 168 | 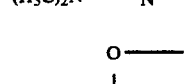 | — | 0 | CO$_2$CH$_3$ | — |
| 169 | 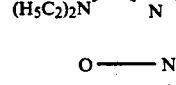 | CH$_2$ | 1 | CO$_2$C$_2$H$_5$ | — |

-continued

| # | Structure | | n | R | X |
|---|---|---|---|---|---|
| 170 | (3-methoxy-1,2,4-oxadiazol-5-yl, CH₃ at C) | — | 0 | OCH₃ | — |
| 171 | (3-methoxy-1,2,4-oxadiazol-5-yl, CH₃ at C) | — | 0 | OC₂H₅ | — |
| 172 | (3-ethoxy-1,2,4-oxadiazol-5-yl, CH₃ at C) | — | 0 | CO₂CH₃ | (5)-Cl |
| 173 | (3-methylthio-1,2,4-oxadiazol-5-yl, CH₃ at C) | — | 0 | CO₂CH₃ | — |
| 174 | (3-chloro-1,2,4-oxadiazol-5-yl, CH₃ at C) | — | 0 | CO₂CH₃ | — |
| 175 | (3-chloro-1,2,4-oxadiazol-5-yl, CH₃ at C) | — | 0 | CO₂C₂H₅ | — |
| 176 | (3-chloro-1,2,4-oxadiazol-5-yl, CH₃ at C) | — | 0 | CO₂CH₃ | (5)-Cl |
| 177 | (3-chloro-1,2,4-oxadiazol-5-yl, CH₃ at C) | CH₂ | 1 | CO₂CH₃ | — |
| 178 | (3-chloro-1,2,4-oxadiazol-5-yl, CH₃ at C) | — | 0 | OCH₃ | — |
| 179 | (3-chloro-1,2,4-oxadiazol-5-yl, CH₃ at C) | — | 0 | OC₂H₅ | — |
| 180 | (3-chloro-1,2,4-oxadiazol-5-yl, CH₃ at C) | — | 0 | OC₃H₇–$n$ | — |
| 181 | (3-chloro-1,2,4-oxadiazol-5-yl, CH₃ at C) | — | 0 | SCH₃ | — |
| 182 | (3-chloro-1,2,4-oxadiazol-5-yl, CH₃ at C) | — | 0 | SC₂H₅ | — |
| 183 | (3-chloro-1,2,4-oxadiazol-5-yl, CH₃ at C) | — | 0 | SOC₂H₅ | — |
| 184 | (3-chloro-1,2,4-oxadiazol-5-yl, CH₃ at C) | — | 0 | SO₂CH₃ | — |

-continued

| # | Structure | Group | n | R | Sub |
|---|---|---|---|---|---|
| 185 | oxadiazole-Cl | — | 0 | Cl | — |
| 186 | oxadiazole-Cl | — | 0 | Br | — |
| 187 | oxadiazole-Cl | — | 0 | Cl | (6)-Cl |
| 188 | oxadiazole-Cl | — | 0 | Cl | (6)-$CH_3$ |
| 189 | oxadiazole-Cl | — | 0 | $OCF_3$ | — |
| 190 | oxadiazole-Cl | — | 0 | $OCHF_2$ | — |
| 191 | oxadiazole-Cl | — | 0 | CN | — |
| 192 | oxadiazole-Cl | $CH_2$ | 1 | $OCHF_2$ | — |
| 193 | oxadiazole-Cl | — | 0 | $CH_3$ | — |
| 194 | oxadiazole-Cl | — | 0 | $C_6H_5$ | — |
| 195 | oxadiazole-Br | $CH_2$ | 1 | $CO_2CH_3$ | — |
| 196 | oxadiazole-Br | — | 0 | $CO_2C_2H_5$ | — |
| 197 | oxadiazole-Br | — | 0 | $CO_2C_3H_7-i$ | — |
| 198 | oxadiazole-Br | — | 0 | $CO_2CH_2CH_2OCH_3$ | — |
| 199 | oxadiazole-Br | — | 0 | $CO_2CH_3$ | (5)-Cl |

-continued

| No. | Structure | | n | R | R' |
|---|---|---|---|---|---|
| 200 | Br-C(=N)-O-N=C(CH₃) oxadiazole | — | 0 | OCF₃ | — |
| 201 | " | — | 0 | OCHF₂ | — |
| 202 | " | — | 0 | OCH₃ | — |
| 203 | " | — | 0 | OC₂H₅ | — |
| 204 | " | — | 0 | OC₃H₇ | — |
| 205 | " | — | 0 | Cl | — |
| 206 | " | CH₂ | 1 | Cl | — |
| 207 | " | — | 0 | Cl | (6)-Cl |
| 208 | " | — | 0 | Br | — |
| 209 | " | — | 0 | F | — |
| 210 | " | — | 0 | SCH₃ | — |
| 211 | " | — | 0 | SC₂H₅ | — |
| 212 | " | — | 0 | SC₃H₇-n | — |
| 213 | " | — | 0 | SOC₂H₅ | — |
| 214 | " | — | 0 | SO₂C₂H₅ | — |

| # | Structure | | | |
|---|---|---|---|---|
| 215 | 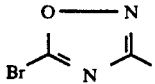 | — | O | 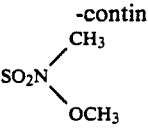 | — |
| 216 | 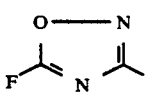 | — | O | CO₂CH₃ | — |
| 217 | 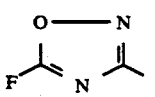 | — | O | Cl | — |
| 218 | 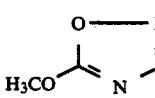 | — | O | Cl | — |
| 219 | 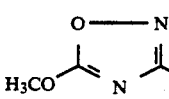 | — | O | C₆H₅ | — |
| 220 | 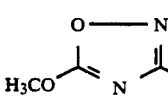 | — | O | SCH₃ | — |
| 221 | 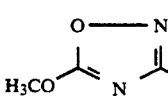 | — | O | SO₂C₂H₅ | — |
| 222 | 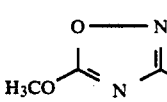 | — | O | OCF₃ | — |
| 223 | 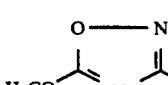 | — | O | SO₂N(CH₃)₂ | — |
| 224 | 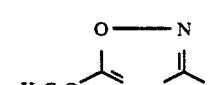 | — | O | CO₂CH₃ | — |
| 225 | 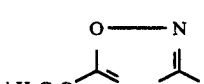 | — | O | CO₂CH₃ | — |
| 226 | 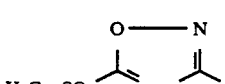 | — | O | CO₂CH₃ | — |
| 227 | 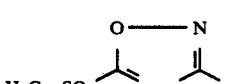 | — | O | CO₂C₂H₅ | — |
| 228 | 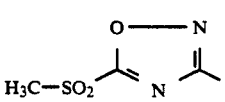 | — | O | CO₂C₂H₅ | (5)-Cl |
| 229 | 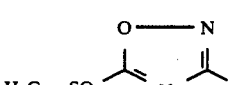 | — | O | CO₂CH₃ | — |

-continued

| # | Structure | | | R | Other |
|---|---|---|---|---|---|
| 230 | H₃C-SO-C(=N-O-)-N=C(CH₃)- | — | 0 | CO₂C₂H₅ | — |
| 231 | H₃C-NH-C(=N-O-)-N=C(CH₃)- | — | 0 | CO₂CH₃ | — |
| 232 | H₃C-NH-C(=N-O-)-N=C(CH₃)- | — | 0 | CO₂CH₃ | — |
| 233 | H₃C-NH-C(=N-O-)-N=C(CH₃)- | — | 0 | Cl | — |
| 234 | H₅C₂-NH-C(=N-O-)-N=C(CH₃)- | — | 0 | Cl | (6)-Cl |
| 235 | H₅C₂-NH-C(=N-O-)-N=C(CH₃)- | — | 0 | Cl | (6)-CH₃ |
| 236 | H₅C₂-NH-C(=N-O-)-N=C(CH₃)- | — | 0 | OC₂H₅ | — |
| 237 | n-H₇C₃-NH-C(=N-O-)-N=C(CH₃)- | — | 0 | CO₂CH₃ | — |
| 238 | H₃C-NH-C(=N-O-)-N=C(CH₃)- | — | 0 | OCF₃ | — |
| 239 | F₂CH-C(=N-O-)-N=C(CH₃)- | — | 0 | CO₂CH₃ | — |
| 240 | Cl₂CH-C(=N-O-)-N=C(CH₃)- | — | 0 | CO₂CH₃ | — |
| 241 | Br₂CH-C(=N-O-)-N=C(CH₃)- | — | 0 | CO₂CH₃ | — |
| 242 | H₅C₂O-C(=N-O-)-N=C(CH₃)- | — | 0 | CO₂CH₃ | — |
| 243 | H₅C₂S-C(=N-O-)-N=C(CH₃)- | — | 0 | CO₂C₂H₅ | — |
| 244 | (C₂H₅)₂N-C(=N-O-)-N=C(CH₃)- | — | 0 | CO₂CH₃ | — |

-continued
| | | | | | |
|---|---|---|---|---|---|
| 245 | 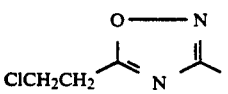 | — | 0 | CO₂CH₃ | — |
| 246 | 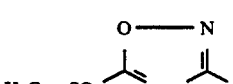 | — | 0 | CO₂CH₃ | — |
| 247 | 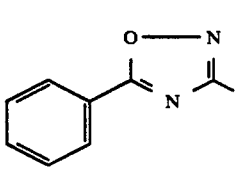 | — | 0 | CO₂CH₃ | (6-)Cl |
| 248 | 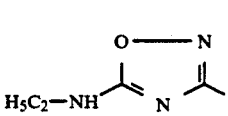 | — | 0 | CO₂CH₃ | — |
| 249 | 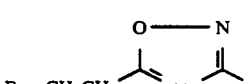 | — | 0 | CO₂CH₃ | — |
| 250 | 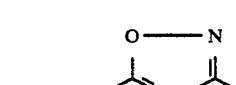 | — | 0 | CO₂CH₃ | — |
| 251 | 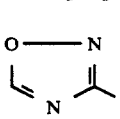 | CH₂ | 1 | CO₂CH₃ | — |
| 252 | 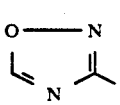 | CH₂ | 1 | CO₂C₂H₅ | — |
| 253 | 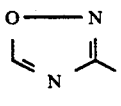 | — | 0 | CO₂C₃H₇-n | — |
| 254 | 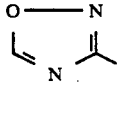 | — | 0 | CO₂C₃H₇-i | — |
| 255 | 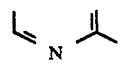 | CH₂ | 1 | OCF₃ | — |
| 256 | 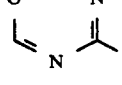 | — | 0 | CO₂CH₃ | (5)-Cl |
| 257 | 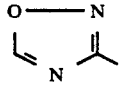 | — | 0 | Cl | — |
| 258 | 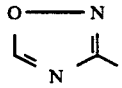 | — | 0 | Br | — |
| 259 | 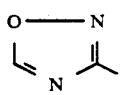 | — | 0 | F | — |

| | | | | | |
|---|---|---|---|---|---|
| 260 | oxadiazole | — | 0 | Cl | (6)-Cl |
| 261 | oxadiazole | — | 0 | Cl | (6)-CH$_3$ |
| 262 | oxadiazole | CH$_2$ | 1 | OCH$_3$ | — |
| 263 | oxadiazole | CH$_2$ | 1 | OC$_2$H$_5$ | — |
| 264 | oxadiazole | — | 0 | CF$_3$ | — |
| 265 | oxadiazole | — | 0 | OCF$_3$ | — |
| 266 | oxadiazole | — | 0 | OCHF$_2$ | — |
| 267 | oxadiazole | — | 0 | CH$_3$ | — |
| 268 | oxadiazole | — | 0 | SO$_2$N(CH$_3$)$_2$ | — |
| 269 | oxadiazole | — | 0 | SCH$_3$ | — |
| 270 | oxadiazole | — | 0 | SOCH$_3$ | — |
| 271 | oxadiazole | — | 0 | SO$_2$CH$_3$ | — |
| 272 | oxadiazole | — | 0 | Cl | (6-)F |
| 273 | oxadiazole | — | 0 | SOC$_2$H$_5$ | — |
| 274 | oxadiazole | — | 0 | SO$_2$C$_2$H$_5$ | — |

| | | | | |
|---|---|---|---|---|
| 275 | 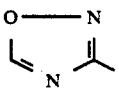 | — | 0 | $SC_3H_{7-n}$ | — |
| 276 | 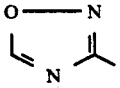 | — | 0 | $SOC_3H_{7-n}$ | — |
| 277 | 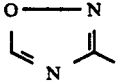 | — | 0 | $SO_2C_3H_{7-n}$ | — |
| 278 | 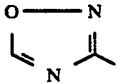 | $CH_2$ | 1 | $SO_2N(CH_3)_2$ | — |
| 279 | 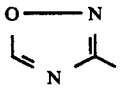 | — | 0 | $SO_2N\begin{smallmatrix}CH_3\\OCH_3\end{smallmatrix}$ | — |
| 280 | 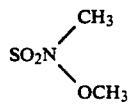 | $CH_2$ | 1 | $CH_3$ | — |
| 281 | 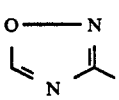 | — | 0 | $CO_2CH_3$ | — |
| 282 | 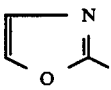 | — | 0 | $CO_2CH_3$ | (6)-Cl |
| 283 | 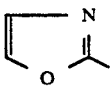 | — | 0 | $OCH_3$ | — |
| 284 | 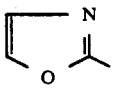 | — | 0 | $OC_2H_5$ | — |
| 285 | 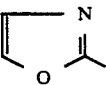 | — | 0 | Cl | — |
| 286 | 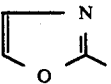 | — | 0 | Cl | (6)-Cl |
| 287 | 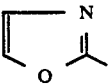 | — | 0 | $SCH_3$ | — |
| 288 | 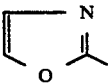 | — | 0 | $SC_3H_7$ | — |
| 289 | 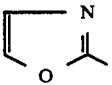 | — | 0 | $SOC_2H_5$ | — |

| | | | | |
|---|---|---|---|---|
| 290 | oxazole (H at 4,5; attach at 2) | — | O | SO$_2$C$_2$H$_5$ | — |
| 291 | oxazole | — | O | OCF$_3$ | — |
| 292 | oxazole | — | O | C$_6$H$_5$ | — |
| 293 | oxazole | — | O | OCF$_3$ | — |
| 294 | oxazole | — | O | OCHF$_2$ | — |
| 295 | 4-C$_2$H$_5$-oxazole | — | O | CO$_2$CH$_3$ | — |
| 296 | 4-i-C$_3$H$_7$-oxazole | — | O | CO$_2$C$_2$H$_5$ | — |
| 297 | 4-n-C$_3$H$_7$-oxazole | — | O | CO$_2$CH$_3$ | — |
| 298 | 4-CH$_3$-oxazole | — | O | SCH$_3$ | — |
| 299 | 4-C$_2$H$_5$-oxazole | — | O | SC$_2$H$_5$ | — |
| 300 | 4-C(CH$_3$)$_3$-oxazole | — | O | SOC$_2$H$_5$ | — |
| 301 | 4-CH$_3$-oxazole | — | O | SO$_2$C$_2$H$_5$ | — |
| 302 | 4-CH$_3$-oxazole | — | O | C$_6$H$_5$ | — |
| 303 | 4-CF$_3$-oxazole | — | O | CO$_2$CH$_3$ | — |
| 304 | 4-CF$_3$-oxazole | — | O | OCH$_3$ | — |
| 305 | 4-CF$_3$-oxazole | — | O | Cl | — |

| | | | | | |
|---|---|---|---|---|---|
| 306 | 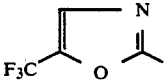 | — | 0 | OEt | — |
| 307 |  | — | 0 | OCF$_3$ | — |
| 308 |  | — | 0 | SC$_2$H$_5$ | — |
| 309 |  | — | 0 | Cl | (6)-CH$_3$ |
| 310 |  | — | 0 | CO$_2$CH$_3$ | — |
| 311 | 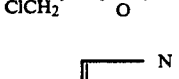 | — | 0 | CO$_2$C$_3$H$_7$-$i$ | — |
| 312 | 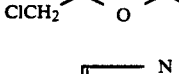 | — | 0 | CO$_2$CH$_3$ | (5)-Cl |
| 313 | 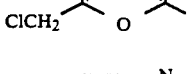 | — | 0 | OCH$_3$ | — |
| 314 | 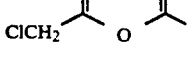 | — | 0 | SC$_2$H$_5$ | — |
| 315 | 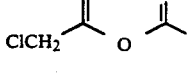 | CH$_2$ | 1 | CO$_2$CH$_3$ | — |
| 316 | 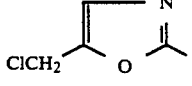 | — | 0 | C$_6$H$_5$ | — |
| 317 | 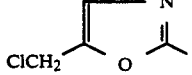 | — | 0 | CO$_2$CH$_3$ | — |
| 318 | 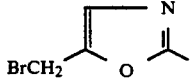 | — | 0 | CO$_2$CH$_3$ | — |
| 319 | 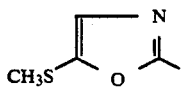 | — | 0 | CO$_2$C$_2$H$_5$ | — |
| 320 | 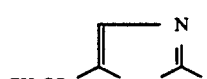 | — | 0 | CO$_2$CH$_3$ | — |

-continued

| | | | | | |
|---|---|---|---|---|---|
| 321 | H3C-[oxazole]- | — | 0 | CO2CH3 | (6-)-Cl |
| 322 | H3C-[oxazole]- | — | 0 | OCH3 | — |
| 323 | H3C-[oxazole]- | — | 0 | OC2H5 | — |
| 324 | H3C-[oxazole]- | — | 0 | Cl | — |
| 325 | H3C-[oxazole]- | — | 0 | Cl | (6)-Cl |
| 326 | H3C-[oxazole]- | — | 0 | SO2N(CH3)2 | — |
| 327 | H3C-[oxazole]- | — | 0 | SCH3 | — |
| 328 | H3C-[oxazole]- | — | 0 | SC2H5 | — |
| 329 | H3C-[oxazole]- | — | 0 | OCHF2 | — |
| 330 | H3C-[oxazole]- | — | 0 | SO2CH3 | — |
| 331 | H3C-[oxazole]- | — | 0 | C6H5 | — |
| 332 | H2C5-[oxazole]- | — | 0 | CO2CH3 | — |
| 333 | H2C5-[oxazole]- | — | 0 | CO2C2H5 | — |
| 334 | H2C5-[oxazole]- | — | 0 | F | — |

| No. | R | — | n | X | Y |
|---|---|---|---|---|---|
| 335 | H₂C₅-[oxazole] | — | 0 | Cl | — |
| 336 | H₂C₅-[oxazole] | — | 0 | OC₂H₅ | — |
| 337 | H₂C₅-[oxazole] | — | 0 | OCH₃ | — |
| 338 | H₂C₅-[oxazole] | — | 0 | OC₃H₇ | — |
| 339 | H₂C₅-[oxazole] | — | 0 | SCH₃ | — |
| 340 | H₂C₅-[oxazole] | — | 0 | SO₂C₂H₅ | — |
| 341 | H₂C₅-[oxazole] | — | 0 | OCF₃ | — |
| 342 | H₂C₅-[oxazole] | — | 0 | OCHF₂ | — |
| 343 | ClCH₂-[oxazole] | — | 0 | CO₂CH₃ | — |
| 344 | ClCH₂-[oxazole] | — | 0 | CF₃ | — |
| 345 | ClCH₂-[oxazole] | — | 0 | Cl | (6)-Cl |
| 346 | ClCH₂-[oxazole] | — | 0 | OCH₃ | — |
| 347 | ClCH₂-[oxazole] | — | 0 | OC₂H₅ | — |
| 348 | ClCH₂-[oxazole] | — | 0 | SCH₃ | — |

-continued

| # | R | | | | |
|---|---|---|---|---|---|
| 349 | ClCH₂-oxazole | — | 0 | SO—C₂H₅ | — |
| 350 | ClCH₂-oxazole | — | 0 | SO₂C₃H₇-n | — |
| 351 | BrCH₂-oxazole | — | 0 | CO₂CH₃ | — |
| 352 | BrCH₂-oxazole | — | 0 | C₆H₅ | — |
| 353 | BrCH₂-oxazole | — | 0 | CO₂CH₂CH₂Cl | — |
| 354 | i-H₇C₃-oxazole | — | 0 | CO₂CH₃ | — |
| 355 | i-H₇C₃-oxazole | — | 0 | CO₂C₃H₇-n | — |
| 356 | n-H₇C₃-oxazole | — | 0 | CO₂CH₃ | — |
| 357 | F₃C-oxazole | — | 0 | CO₂CH₃ | — |
| 358 | H₃CO-oxazole | — | 0 | CO₂CH₃ | — |
| 359 | H₅C₂S-oxazole | — | 0 | CO₂CH₃ | — |
| 360 | (H₃C)₂N-oxazole | — | 0 | CO₂C₂H₅ | — |
| 361 | Br,H₃C-oxazole | — | 0 | CO₂CH₃ | — |
| 362 | Br,H₃C-oxazole | — | 0 | OC₂H₅ | — |

| No. | Structure | | | Substituent | |
|---|---|---|---|---|---|
| 363 | Br, H₃C oxazole | — | 0 | OCF₃ | — |
| 364 | Br, H₅C₂ oxazole | — | 0 | SO₂N(CH₃)(OCH₃) | — |
| 365 | Cl, H₃C oxazole | — | 0 | CO₂CH₃ | — |
| 366 | Cl, H₅C₂ oxazole | — | 0 | CO₂CH₃ | (5)-Cl |
| 367 | Cl, H₅C₂ oxazole | — | 0 | SC₂H₅ | — |
| 368 | F₃C, H₃C oxazole | — | 0 | CO₂CH₃ | — |
| 369 | F₃C, H₃C oxazole | — | 0 | Br | — |
| 370 | H₃C, F₃C oxazole | — | 0 | OC₂H₅ | — |
| 371 | H₃CS, H₃C oxazole | — | 0 | CO₂CH₃ | — |
| 372 | H₅C₂, H₃C oxazole | — | 0 | CO₂CH₃ | (6)-Cl |
| 373 | Cl, Cl oxazole | — | 0 | CO₂CH₃ | — |
| 374 | Cl, Br oxazole | — | 0 | CO₂CH₃ | — |
| 375 | Br, Br oxazole | — | 0 | CO₂C₂H₅ | — |
| 376 | oxazole | — | 0 | CO₂CH₃ | — |

| No. | Het | | n | R | X |
|---|---|---|---|---|---|
| 377 | oxazol-4-yl | — | 0 | OCHF$_2$ | — |
| 378 | oxazol-4-yl | — | 0 | Cl | — |
| 379 | oxazol-4-yl | — | 0 | OC$_2$H$_5$ | — |
| 380 | oxazol-4-yl | — | 0 | SCH$_3$ | — |
| 381 | oxazol-4-yl | — | 0 | SO$_2$C$_2$H$_5$ | — |
| 382 | oxazol-4-yl | — | 0 | CF$_3$ | — |
| 383 | oxazol-4-yl | — | 0 | C$_6$H$_5$ | — |
| 384 | oxazol-4-yl | — | 0 | CO$_2$CH$_3$ | (5)-Cl |
| 385 | 2-CH$_3$-oxazol-4-yl | — | 0 | CO$_2$CH$_3$ | (5)-Cl |
| 386 | 2-CH$_3$-oxazol-4-yl | — | 0 | CO$_2$C$_2$H$_5$ | — |
| 387 | 2-CH$_3$-oxazol-4-yl | — | 0 | OCH$_3$ | — |
| 388 | 2-CH$_3$-oxazol-4-yl | — | 0 | SC$_2$H$_5$ | — |
| 389 | 2-CH$_3$-oxazol-4-yl | — | 0 | SO$_2$C$_2$H$_5$ | — |
| 390 | 2-CH$_3$-oxazol-4-yl | — | 0 | OC$_2$H$_5$ | — |
| 391 | 2-CH$_3$-oxazol-4-yl | — | 0 | OCF$_3$ | — |

| | | | | | |
|---|---|---|---|---|---|
| 392 | 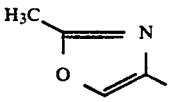 | — | 0 | C$_6$H$_5$ | — |
| 393 | 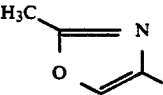 | — | 0 | Cl | — |
| 394 | 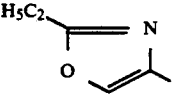 | — | 0 | CO$_2$CH$_3$ | — |
| 395 | 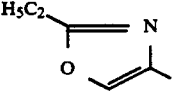 | — | 0 | SCH$_3$ | — |
| 396 | 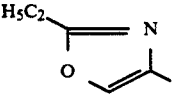 | — | 0 | SO$_2$C$_3$H$_{7-n}$ | — |
| 397 | 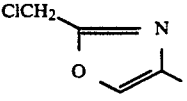 | — | 0 | CO$_2$CH$_3$ | — |
| 398 | 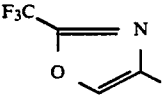 | — | 0 | CO$_2$CH$_3$ | — |
| 399 | 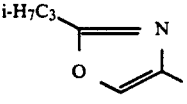 | — | 0 | OCH$_3$ | — |
| 400 | 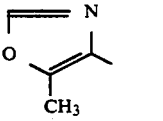 | — | 0 | CO$_2$CH$_3$ | — |
| 401 | 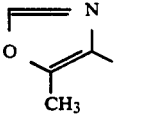 | — | 0 | CO$_2$C$_2$H$_5$ | — |
| 402 | 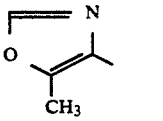 | — | 0 | OC$_3$H$_{7-i}$ | — |
| 403 | 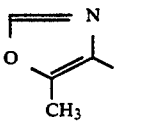 | — | 0 | SCH$_3$ | — |
| 404 | 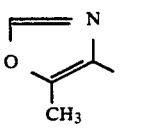 | — | 0 | SO$_2$C$_3$H$_{7-n}$ | — |

-continued

| | | | | | |
|---|---|---|---|---|---|
| 405 | isoxazole-CH₃ | — | O | SO₂N(CH₃)₂ | — |
| 406 | isoxazole-CH₃ | — | O | Cl | — |
| 407 | isoxazole-CH₃ | — | O | Cl | (6)-CH₃ |
| 408 | isoxazole-C₂H₅ | — | O | CO₂CH₃ | — |
| 409 | isoxazole-C₂H₅ | — | O | CO₂CH₃ | (6)-Cl |
| 410 | isoxazole-C₂H₅ | — | O | OCF₃ | — |
| 411 | isoxazole-C₂H₅ | — | O | C₆H₅ | — |
| 412 | isoxazole-C₃H₇-n | — | O | CO₂CH₃ | — |
| 413 | isoxazole-C₄H₉-n | — | O | CO₂C₂H₅ | — |
| 414 | isoxazole-CH₂Cl | — | O | CO₂CH₃ | (5)-Cl |
| 415 | isoxazole-CF₃ | — | O | CO₂CH₂CH₂Cl | — |
| 416 | isoxazole-CHF₂ | — | O | OC₂H₅ | — |

| | | | | | |
|---|---|---|---|---|---|
| 417 | 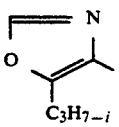 | — | 0 | SOC$_2$H$_5$ | — |
| 418 | 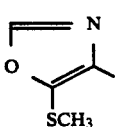 | — | 0 | CO$_2$CH$_3$ | — |
| 419 | 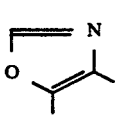 | — | 0 | CO$_2$CH$_3$ | — |
| 420 | 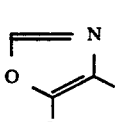 | — | 0 | CO$_2$C$_2$H$_5$ | — |
| 421 | 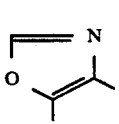 | — | 0 | CO$_2$CH$_3$ | — |
| 422 | 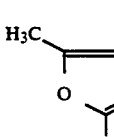 | — | 0 | CO$_2$CH$_3$ | — |
| 423 | 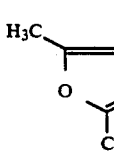 | — | 0 | OC$_2$H$_5$ | — |
| 424 | 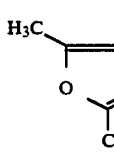 | — | 0 | OCH$_2$CH$_2$Cl | — |
| 425 | 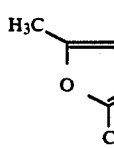 | — | 0 | CO$_2$CH$_3$ | — |
| 426 | 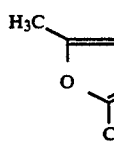 | — | 0 | SO$_2$C$_2$H$_5$ | — |
| 427 | 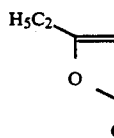 | — | 0 | Cl | — |

| | | | | | |
|---|---|---|---|---|---|
| 428 | 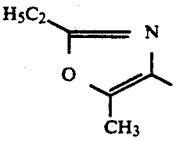 | — | O | Cl | (6)-Cl |
| 429 | 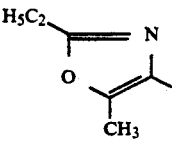 | — | O | OCF₃ | — |
| 430 | 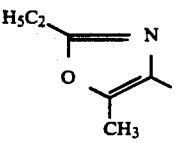 | — | O | CO₂CH₃ | — |
| 431 | 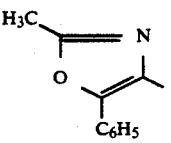 | — | O | CO₂CH₃ | — |
| 432 | 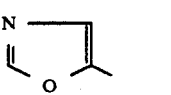 | — | O | CO₂CH₃ | — |
| 433 | 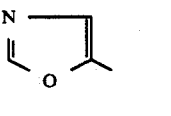 | — | O | CF₃ | — |
| 434 | 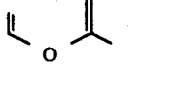 | — | O | OC₃H₇ | — |
| 435 | 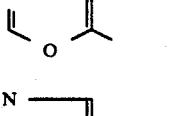 | — | O | SCH₃ | — |
| 436 | 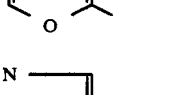 | — | O | SO₂C₃H₇₋ᵢ | — |
| 437 | 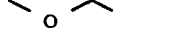 | — | O | Cl | (6)-CH₃ |
| 438 | 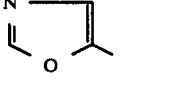 | — | O | C₆H₅ | — |
| 439 | 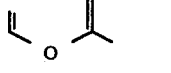 | — | O | OCF₃ | — |
| 440 | 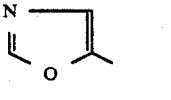 | — | O | CO₂CH₃ | (5)-Cl |
| 441 | 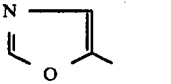 | — | O | F | — |

-continued
| | | | | | |
|---|---|---|---|---|---|
| 442 | 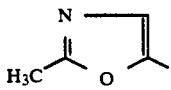 | — | 0 | CO$_2$CH$_3$ | — |
| 443 | 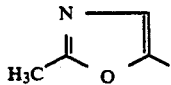 | — | 0 | Br | — |
| 444 | 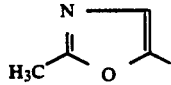 | — | 0 | OC$_3$H$_7$-$i$ | — |
| 445 | 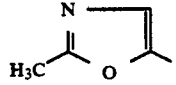 | — | 0 | SC$_3$H$_7$-$i$ | — |
| 446 | 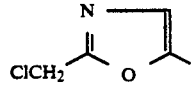 | — | 0 | CO$_2$CH$_3$ | — |
| 447 | 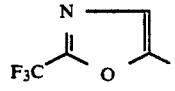 | — | 0 | CO$_2$CH$_3$ | — |
| 448 | 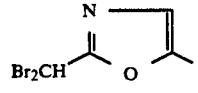 | — | 0 | CO$_2$C$_2$H$_5$ | — |
| 449 | 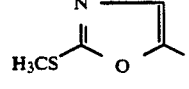 | — | 0 | SO$_2$C$_2$H$_5$ | — |
| 450 | 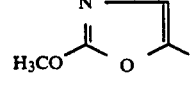 | — | 0 | CO$_2$CH$_3$ | — |
| 451 | 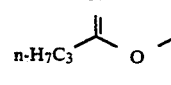 | — | 0 | C$_6$H$_5$ | — |
| 452 | 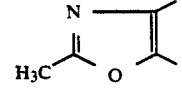 | — | 0 | CO$_2$CH$_3$ | — |
| 453 | 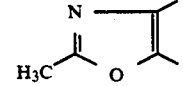 | — | 0 | OC$_2$H$_5$ | — |
| 454 | 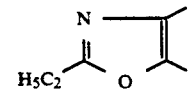 | — | 0 | OCF$_3$ | — |
| 455 | 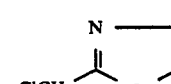 | — | 0 | OCHF$_2$ | — |
| 456 | 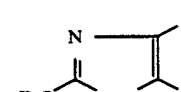 | — | 0 | C$_6$H$_5$ | — |

-continued

| # | Structure | | | | |
|---|---|---|---|---|---|
| 457 | oxazoline with n-H7C3, CH3, CH3 | — | 0 | CO2CH3 | (5)-Cl |
| 458 | oxazoline with H3C, C2H5, CH3 | — | 0 | CH3 | — |
| 459 | oxazoline with H3CO, C2H5, CH3 | — | 0 | SCH3 | — |
| 460 | oxazoline with H5C2, C2H5, CH3 | — | 0 | SO2C2H5 | — |
| 461 | oxazoline with Br, CH3, CH3 | — | 0 | SO2N(CH3)2 | — |
| 462 | thiazole | — | 0 | CO2CH3 | — |
| 463 | thiazole | — | 0 | CO2C3H7-n | — |
| 464 | thiazole | — | 0 | Cl | (6)-CH3 |
| 465 | thiazole | — | 0 | OCH3 | — |
| 466 | thiazole | — | 0 | OC2H5 | — |
| 467 | thiazole | — | 0 | OCF3 | — |
| 468 | thiazole | — | 0 | OCHF2 | — |
| 469 | thiazole | — | 0 | SCH3 | — |
| 470 | thiazole | — | 0 | SC2H5 | — |
| 471 | thiazole | — | 0 | SOC3H7 | — |

| | | | | | |
|---|---|---|---|---|---|
| 472 | [thiazole-CH3] | — | 0 | SOC$_2$H$_5$ | — |
| 473 | [thiazole-CH3] | — | 0 | SO$_2$CH$_3$ | — |
| 474 | [thiazole-CH3] | — | 0 | Br | — |
| 475 | [thiazole-CH3] | — | 0 | CF$_3$ | — |
| 476 | [thiazole-CH3] | NH | 1 | Cl | — |
| 477 | [4-methylthiazole-CH3] | — | 0 | CO$_2$CH$_3$ | (5)-Cl |
| 478 | [4-methylthiazole-CH3] | — | 0 | Cl | (6)-Cl |
| 479 | [4-methylthiazole-CH3] | — | 0 | OC$_3$H$_{7-n}$ | — |
| 480 | [4-methylthiazole-CH3] | — | 0 | OCF$_3$ | — |
| 481 | [4-methylthiazole-CH3] | — | 0 | SC$_2$H$_5$ | — |
| 482 | [4-ethylthiazole-CH3] | — | 0 | CO$_2$CH$_3$ | — |
| 483 | [4-ethylthiazole-CH3] | — | 0 | CO$_2$C$_3$H$_{7-n}$ | — |
| 484 | [4-ethylthiazole-CH3] | — | 0 | CO$_2$CH$_3$ | (6)-Cl |
| 485 | [4-ethylthiazole-CH3] | — | 0 | CO$_2$CH$_3$ | (5)-Cl |
| 486 | [4-ethylthiazole-CH3] | — | 0 | OCF$_3$ | — |
| 487 | [4-ethylthiazole-CH3] | — | 0 | OC$_2$H$_5$ | — |

-continued

| | | | | | |
|---|---|---|---|---|---|
| 488 | (thiazine with H5C2-S) | — | 0 | SC2H5 | — |
| 489 | (thiazine with n-H7C3-S) | — | 0 | CO2CH3 | — |
| 490 | (thiazine with n-H7C3-S) | — | 0 | Cl | (6)-CH3 |
| 491 | (thiazine with n-H7C3-S) | — | 0 | SO2C2H5 | — |
| 492 | (thiazine with i-H7C3-S) | — | 0 | CO2C2H5 | — |
| 493 | (thiazine with n-H9C4-S) | — | 0 | CO2CH3 | — |
| 494 | (thiazine with t-H9C4-S) | — | 0 | CO2CH3 | (5)-Cl |
| 495 | (thiazine with H5C6-S) | — | 0 | CO2CH3 | — |
| 496 | (thiazine with H5C6-S) | — | 0 | OCH3 | — |
| 497 | (thiazine with H5C6-S) | — | 0 | SO2C2H5 | — |
| 498 | (thiazine with ClCH2-S) | — | 0 | CO2CH3 | — |
| 499 | (thiazine with ClCH2-S) | — | 0 | C6H5 | — |
| 500 | (thiazine with ClCH2-S) | — | 0 | SC3H7−n | — |
| 501 | (thiazine with ClCH2-S) | — | 0 | Br | — |
| 502 | (thiazine with BrCH2-S) | — | 0 | CO2CH3 | — |

| No. | Structure | Linker | n | R | Extra |
|---|---|---|---|---|---|
| 503 | BrCH$_2$-thiazole | CH$_2$ | 1 | CO$_2$CH$_3$ | — |
| 504 | BrCH$_2$-thiazole | — | 0 | OCF$_3$ | — |
| 505 | BrCH$_2$-thiazole | — | 0 | CF$_3$ | — |
| 506 | BrCH$_2$-thiazole | — | 0 | SC$_3$H$_7$-$i$ | — |
| 507 | Cl-thiazole | — | 0 | CO$_2$CH$_3$ | — |
| 508 | Cl-thiazole | — | 0 | CH$_3$ | — |
| 509 | Cl-thiazole | O | 1 | CH$_3$ | — |
| 510 | Cl-thiazole | — | 0 | OC$_2$H$_5$ | — |
| 511 | Cl-thiazole | — | 0 | Cl | (6)-CH$_3$ |
| 512 | H$_3$C-thiazole | — | 0 | CO$_2$C$_2$H$_5$ | — |
| 513 | H$_3$C-thiazole | — | 0 | CO$_2$CH$_3$ | (5)-Cl |
| 514 | H$_3$C-thiazole | — | 0 | OCH$_3$ | — |
| 515 | H$_3$C-thiazole | — | 0 | OC$_3$H$_7$-$i$ | — |
| 516 | H$_3$C-thiazole | — | 0 | Cl | — |
| 517 | H$_3$C-thiazole | — | 0 | Cl | (6)-Cl |

| # | Structure | | n | R | X |
|---|---|---|---|---|---|
| 518 | H3C-thiazole | — | 0 | SO2N(CH3)(OCH3) | — |
| 519 | H3C-thiazole | — | 0 | SC2H5 | — |
| 520 | H3C-thiazole | — | 0 | OCHF2 | — |
| 521 | H3C-thiazole | — | 0 | SO2CH3 | — |
| 522 | H3C-thiazole | — | 0 | C6H5 | — |
| 523 | H3C-thiazole | — | 0 | CF3 | — |
| 524 | H3C-thiazole | — | 0 | CH3 | — |
| 525 | H5C2-thiazole | — | 0 | CO2CH3 | — |
| 526 | H5C2-thiazole | — | 0 | CO2CH3 | (5)-Cl |
| 527 | H5C2-thiazole | CH2 | 1 | CO2CH3 | — |
| 528 | H5C2-thiazole | NH | 1 | Cl | — |
| 529 | H5C2-thiazole | — | 0 | Cl | — |
| 530 | i-H7C3-thiazole | — | 0 | OCH3 | — |
| 531 | i-H7C3-thiazole | — | 0 | CO2CH3 | — |

-continued
| | | | | | |
|---|---|---|---|---|---|
| 532 | n-H9C4 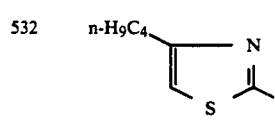 | — | 0 | CO2CH3 | — |
| 533 | t-H9C4 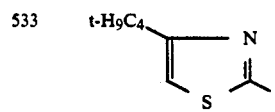 | — | 0 | CO2CH3 | — |
| 534 | ClCH2 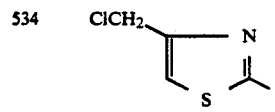 | — | 0 | CO2CH3 | — |
| 535 | ClCH2 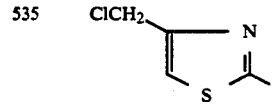 | — | 0 | CF3 | — |
| 536 | ClCH2 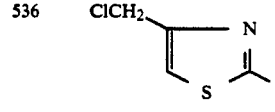 | — | 0 | Cl | (6)-Cl |
| 537 | Cl2CH 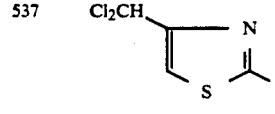 | — | 0 | OC2H5 | — |
| 538 | Cl2CH 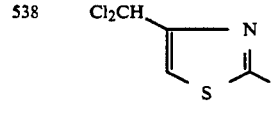 | — | 0 | SCH3 | — |
| 539 | Cl2CH 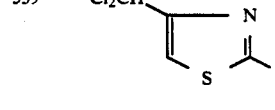 | — | 0 | SO2C2H5 | — |
| 540 | BrCH2 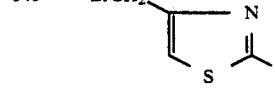 | — | 0 | CO2CH3 | — |
| 541 | BrCH2 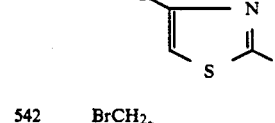 | — | 0 | C6H5 | — |
| 542 | BrCH2 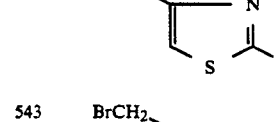 | CH2 | 1 | CO2CH3 | — |
| 543 | BrCH2 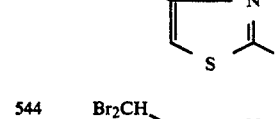 | O | — | OC2H5 | — |
| 544 | Br2CH 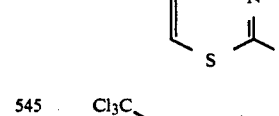 | O | — | SC2H5 | — |
| 545 | Cl3C 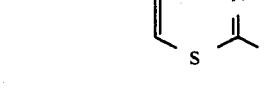 | O | — | CO2CH3 | — |

| | | | | |
|---|---|---|---|---|
| 546 | 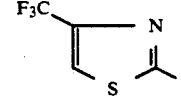 F₃C-thiazole | O | —CO₂CH₃ | — |
| 547 | 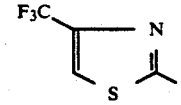 F₃C-thiazole | O | —OCF₃ | — |
| 548 | 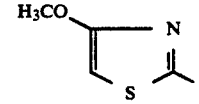 H₃CO-thiazole | O | —CO₂CH₃ | — |
| 549 | 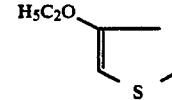 H₅C₂O-thiazole | O | —CO₂C₂H₅ | — |
| 550 | 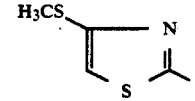 H₃CS-thiazole | O | —CO₂CH₃ | — |
| 551 | 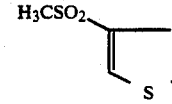 H₃CSO₂-thiazole | O | —OCF₃ | — |
| 552 | 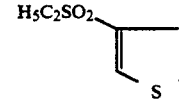 H₅C₂SO₂-thiazole | — | O CO₂CH₃ | — |
| 553 | 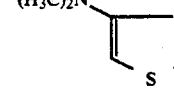 (H₃C)₂N-thiazole | — | O CO₂CH₃ | — |
| 554 | 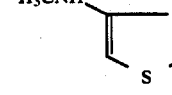 H₃CNH-thiazole | — | O CO₂C₂H₅ | — |
| 555 | 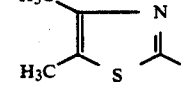 H₃C,H₃C-thiazole | — | O CO₂CH₃ | — |
| 556 | 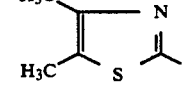 H₃C,H₃C-thiazole | — | O CO₂C₃H₇₋ₙ | — |
| 557 | 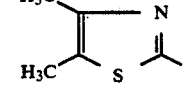 H₃C,H₃C-thiazole | — | O Cl | — |
| 558 | 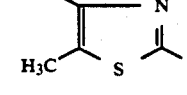 H₃C,H₃C-thiazole | — | O C₆H₅ | — |
| 559 | 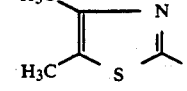 H₃C,H₃C-thiazole | — | O OCH₃ | — |

-continued
| | | | | | |
|---|---|---|---|---|---|
| 560 | 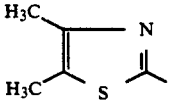 | — | 0 | SC$_2$H$_5$ | — |
| 561 | 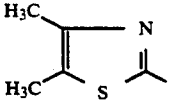 | — | 0 | OCF$_3$ | — |
| 562 | 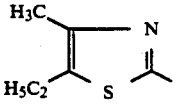 | — | 0 | CO$_2$CH$_3$ | — |
| 563 | 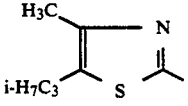 | — | 0 | SCH$_3$ | — |
| 564 | 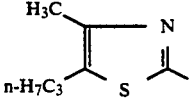 | — | 0 | Cl | (6)-Cl |
| 565 | 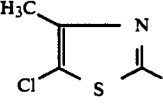 | — | 0 | CO$_2$CH$_3$ | (5)-Cl |
| 566 | 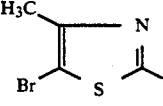 | — | 0 | SC$_2$H$_5$ | — |
| 567 | 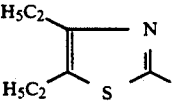 | — | 0 | SO$_2$CH$_3$ | — |
| 568 | 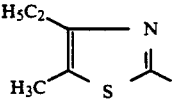 | — | 0 | OC$_2$H$_5$ | — |
| 569 | 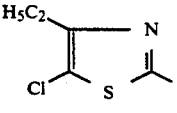 | — | 0 | Br | — |
| 570 | 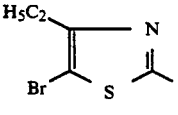 | — | 0 | CO$_2$CH$_2$CH$_2$Cl | — |
| 571 | 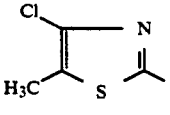 | — | 0 | CF$_3$ | — |
| 572 | 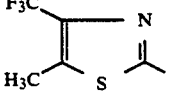 | — | 0 | CO$_2$CH$_3$ | — |
| 573 | 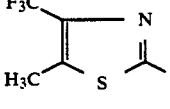 | — | 0 | OC$_2$H$_5$ | — |

| No. | Structure | | | R | Sub |
|---|---|---|---|---|---|
| 574 | H3C-C(=N)-C(CF3)=S (thiazole: 4-CH3, 5-CF3) | — | 0 | CO2C2H5 | — |
| 575 | H3CS-C(=N)-C(CH3)=S (thiazole: 4-SCH3, 5-CH3) | — | 0 | CO2CH3 | (6)-Cl |
| 576 | Cl,Cl-thiazole | — | 0 | CO2CH3 | — |
| 577 | Cl,Cl-thiazole | — | 0 | SC2H5 | — |
| 578 | Cl,Cl-thiazole | — | 0 | OC2H5 | — |
| 579 | Cl,Cl-thiazole | — | 0 | OCF3 | — |
| 580 | Cl,Br-thiazole | — | 0 | C6H5 | — |
| 581 | Br,Br-thiazole | — | 0 | CO2CH3 | — |
| 582 | H3C-thiazole (isomer) | — | 0 | CO2C2H5 | — |
| 583 | H3C-thiazole (isomer) | — | 0 | CO2CH3 | (5)-Cl |
| 584 | H3C-thiazole (isomer) | — | 0 | OC2H5 | — |
| 585 | H3C-thiazole (isomer) | — | 0 | OCH2CH2Cl | — |
| 586 | H3C-thiazole (isomer) | — | 0 | SC2H5 | — |
| 587 | H3C-thiazole (isomer) | — | 0 | SO2C2H5 | — |

-continued
| | | | | | |
|---|---|---|---|---|---|
| 588 | 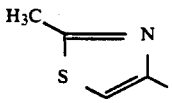 | — | 0 | OCF₃ | — |
| 589 | 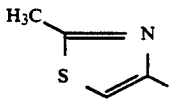 | — | 0 | Br | — |
| 590 | 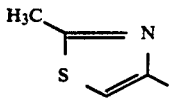 | — | 0 | SOC₃H₇-n | — |
| 591 | 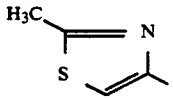 | CH₂ | 1 | CO₂CH₃ | — |
| 592 | 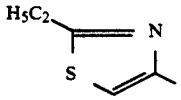 | — | 0 | CO₂CH₃ | — |
| 593 | 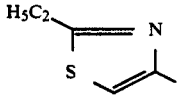 | — | 0 | SCH₃ | — |
| 594 | 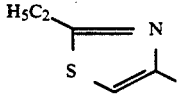 | — | 0 | SO₂C₃H₇-n | — |
| 595 | 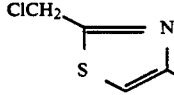 | — | 0 | CO₂CH₃ | — |
| 596 | 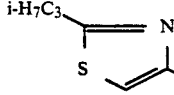 | — | 0 | OCH₃ | — |
| 597 | 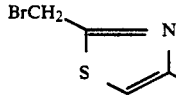 | — | 0 | CO₂CH₃ | — |
| 598 | 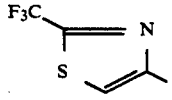 | — | 0 | CO₂CH₃ | — |
| 599 | 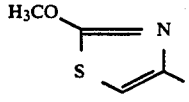 | — | 0 | CO₂CH₃ | (5)-Cl |
| 600 | 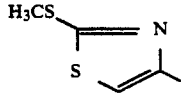 | — | 0 | CO₂C₂H₅ | — |
| 601 | 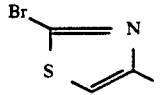 | — | 0 | OC₂H₅ | — |

-continued
| | | | | | |
|---|---|---|---|---|---|
| 602 | 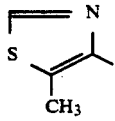 | — | 0 | CO$_2$CH$_3$ | — |
| 603 | 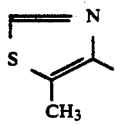 | — | 0 | Cl | — |
| 604 | 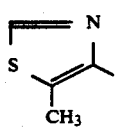 | — | 0 | OC$_2$H$_5$ | — |
| 605 | 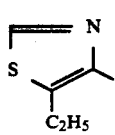 | — | 0 | C$_6$H$_5$ | — |
| 606 | 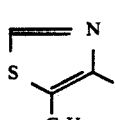 | — | 0 | SCH$_3$ | — |
| 607 | 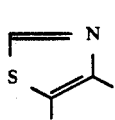 | — | 0 | SO$_2$N(CH$_3$)$_2$ | — |
| 608 | 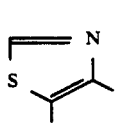 | — | 0 | OCF$_3$ | — |
| 609 | 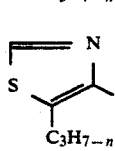 | — | 0 | SO$_2$C$_3$H$_{7-n}$ | — |
| 610 | 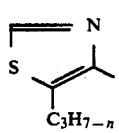 | — | 0 | CO$_2$CH$_3$ | — |
| 611 | 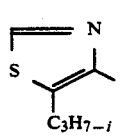 | — | 0 | Cl | (6)-Cl |
| 612 | 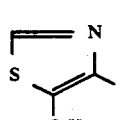 | — | 0 | CO$_2$CH$_3$ | — |
| 613 | 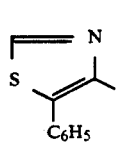 | — | 0 | CO$_2$C$_2$H$_5$ | — |

| No. | Structure | | n | X | Sub |
|---|---|---|---|---|---|
| 614 | thiazole-SCH3 | — | 0 | OC$_2$H$_5$ | — |
| 615 | thiazole-CH$_2$Cl | — | 0 | CO$_2$CH$_3$ | — |
| 616 | thiazole-CF$_3$ | — | 0 | CO$_2$C$_2$H$_5$ | — |
| 617 | thiazole-Cl | — | 0 | CO$_2$C$_3$H$_7$-n | — |
| 618 | H$_3$C-thiazole-CH$_3$ | — | 0 | CO$_2$CH$_3$ | — |
| 619 | H$_3$C-thiazole-CH$_3$ | — | 0 | CO$_2$CH$_3$ | (6)-Cl |
| 620 | H$_3$C-thiazole-CH$_3$ | — | 0 | F | — |
| 621 | H$_3$C-thiazole-CH$_3$ | CH$_2$ | 1 | Cl | — |
| 622 | H$_3$C-thiazole-CH$_3$ | — | 0 | OCH$_3$ | — |
| 623 | H$_3$C-thiazole-CH$_3$ | — | 0 | SC$_3$H$_7$-i | — |
| 624 | H$_3$C-thiazole-CH$_3$ | — | 0 | SO$_2$C$_2$H$_5$ | — |

| # | Structure | | | | |
|---|---|---|---|---|---|
| 625 | H₅C₂−C(S)=N−C(CH₃)=C(CH₃) (thiazole) | — | 0 | CO₂CH₃ | — |
| 626 | H₅C₂−C(S)=N−C(CH₃)=C(CH₃) (thiazole) | — | 0 | CO₂CH₂CH₂OCH₃ | — |
| 627 | H₅C₂−C(S)=N−C(CH₃)=C(CH₃) (thiazole) | — | 0 | OCF₃ | — |
| 628 | H₃C−C(S)=N−C(CH₃)=C(C₂H₅) (thiazole) | — | 0 | C₆H₅ | — |
| 629 | H₃C−C(S)=N−C(CH₃)=C(C₆H₅) (thiazole) | — | 0 | CO₂CH₃ | — |
| 630 | Cl−C(S)=N−C(CH₃)=C(CH₃) (thiazole) | — | 0 | CO₂CH₃ | — |
| 631 | Cl−C(S)=N−C(CH₃)=C(C₂H₅) (thiazole) | — | 0 | CO₂CH₃ | (5)-Cl |
| 632 | N=CH−S−C(CH₃)= (thiazole) | — | 0 | CO₂CH₃ | |
| 633 | N=CH−S−C(CH₃)= (thiazole) | — | 0 | CF₃ | — |
| 634 | N=CH−S−C(CH₃)= (thiazole) | — | 0 | OC₂H₅ | — |
| 635 | N=CH−S−C(CH₃)= (thiazole) | — | 0 | SCH₃ | — |
| 636 | N=CH−S−C(CH₃)= (thiazole) | — | 0 | SO₂C₂H₅ | — |
| 637 | N=CH−S−C(CH₃)= (thiazole) | — | 0 | Cl | (6)-CH₃ |

| | | | | | |
|---|---|---|---|---|---|
| 638 | 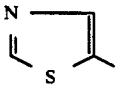 | — | 0 | C₆H₅ | — |
| 639 | 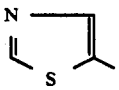 | — | 0 | OCF₃ | — |
| 640 | 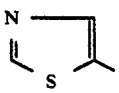 | — | 0 | CO₂CH₃ | (5)-Cl |
| 641 | 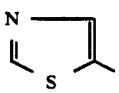 | — | 0 | F | — |
| 642 | 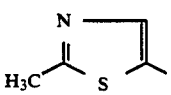 | — | 0 | CO₂CH₃ | — |
| 643 | 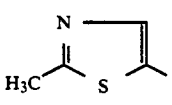 | — | 0 | Br | — |
| 644 | 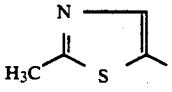 | — | 0 | OC₂H₅ | — |
| 645 | 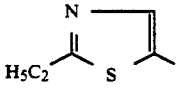 | — | 0 | SC₃H₇-i | — |
| 646 | 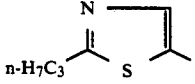 | — | 0 | CO₂CH₃ | — |
| 647 | 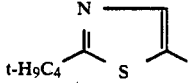 | — | 0 | CO₂CH₃ | — |
| 648 | 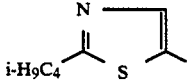 | — | 0 | CO₂C₂H₅ | — |
| 649 | 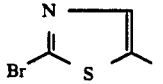 | — | 0 | SO₂C₂H₅ | — |
| 650 | 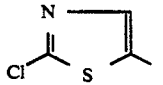 | — | 0 | CO₂CH₃ | (6)-Cl |
| 651 | 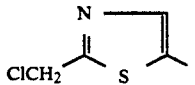 | — | 0 | C₆H₅ | — |
| 652 | 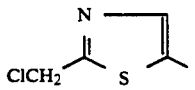 | CH₂ | 1 | Cl | — |

| No. | Structure | | | Substituent | |
|---|---|---|---|---|---|
| 653 | ClCH₂-thiazole-propenyl | — | 0 | OCH₃ | — |
| 654 | BrCH₂-thiazole-propenyl | — | 0 | CO₂CH₃ | — |
| 655 | F₃C-thiazole-propenyl | — | 0 | OC₂H₅ | — |
| 656 | H₃CO-thiazole-propenyl | — | 0 | CO₂CH₃ | — |
| 657 | H₅C₂O-thiazole-propenyl | — | 0 | SO₂C₃H₇₋ₙ | — |
| 658 | H₃CS-thiazole-propenyl | — | 0 | CO₂C₂H₅ | — |
| 659 | H₃CSO₂-thiazole-propenyl | — | 0 | SO₂N(CH₃)₂ | — |
| 660 | (H₃C)₂N-thiazole-propenyl | — | 0 | CO₂CH₃ | — |
| 661 | H₅C₆-thiazole-propenyl | — | 0 | C₆H₅ | — |
| 662 | H₃C-thiazole(CH₃)-propenyl | — | 0 | CO₂CH₃ | — |
| 663 | H₃C-thiazole(CH₃)-propenyl | — | 0 | Cl | — |
| 664 | H₃C-thiazole(CH₃)-propenyl | — | 0 | OCF₃ | — |
| 665 | H₅C₂-thiazole(CH₃)-propenyl | — | 0 | SCH₃ | — |
| 666 | H₃C-thiazole(C₂H₅)-propenyl | — | 0 | SO₂C₂H₅ | — |
| 667 | H₃CO-thiazole(CH₃)-propenyl | — | 0 | C₆H₅ | — |

| No. | Structure | | n | | |
|---|---|---|---|---|---|
| 668 | H3CO-C(=N)-S-C(CH3)=C(CH3) | — | 0 | OC2H5 | — |
| 669 | H3CO-C(=N)-S-C(C2H5)=C(CH3) | — | 0 | Cl | (6)-Cl |
| 670 | Br-C(=N)-S-C(CH3)=C(CH3) | — | 0 | CO2CH3 | — |
| 671 | Cl-C(=N)-S-C(CH3)=C(CH3) | — | 0 | CF3 | — |
| 672 | F3C-C(=N)-S-C(CH3)=C(CH3) | — | 0 | CO2CH3 | — |
| 673 | ClCH2-C(=N)-S-C(CH3)=C(CH3) | — | 0 | OC2H5 | — |
| 674 | Cl2CH-C(=N)-S-C(CH3)=C(CH3) | — | 0 | SC2H5 | — |
| 675 | BrCH2-C(=N)-S-C(CH3)=C(CH3) | — | 0 | Cl | (6)-Cl |
| 676 | H5C6-C(=N)-S-C(CH3)=C(CH3) | — | 0 | SO2N(CH3)2 | — |
| 677 | H3C-C(=N)-S-C(Cl)=C(CH3) | — | 0 | CO2C2H5 | — |
| 678 | H3C-C(=N)-S-C(C6H5)=C(CH3) | — | 0 | C6H5 | — |
| 679 | H3C-C(=N)-S-C(CF3)=C(CH3) | — | 0 | CH3 | — |
| 680 | i-H7C3-C(=N)-S-C(CF3)=C(CH3) | — | 0 | OCF3 | — |
| 681 | H5C2-C(=N)-S-C(C6H5)=C(CH3) | CH2 | 1 | CO2CH3 | — |

-continued

| # | Het | X | n | R | sub |
|---|---|---|---|---|---|
| 682 | oxadiazole | — | 0 | $CO_2CH_3$ | — |
| 683 | oxadiazole | — | 0 | $CO_2CH_3$ | (5)-Cl |
| 684 | oxadiazole | — | 0 | $CO_2CH_3$ | (6)-Cl |
| 685 | oxadiazole | — | 0 | $OC_2H_5$ | — |
| 686 | oxadiazole | — | 0 | $SC_2H_5$ | — |
| 687 | oxadiazole | — | 0 | $SOC_3H_{7-n}$ | — |
| 688 | oxadiazole | — | 0 | Cl | — |
| 689 | oxadiazole | $CH_2$ | 1 | Cl | — |
| 690 | oxadiazole | — | 0 | $OCHF_2$ | — |
| 691 | oxadiazole | — | 0 | $OCF_3$ | — |
| 692 | oxadiazole | — | 0 | $SO_2C_2H_5$ | — |
| 693 | oxadiazole | — | 0 | $CO_2C_2H_5$ | — |
| 694 | oxadiazole | — | 0 | $CF_3$ | — |
| 695 | oxadiazole | — | 0 | $CH_3$ | — |
| 696 | oxadiazole | — | 0 | $C_6H_5$ | — |

| | | | | | |
|---|---|---|---|---|---|
| 697 | 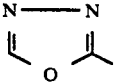 | — | 0 | SO$_2$N(CH$_3$)$_2$ | — |
| 698 | 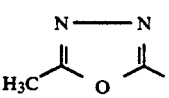 | — | 0 | CO$_2$CH$_3$ | (5)-Cl |
| 699 | 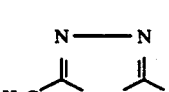 | — | 0 | OCF$_3$ | — |
| 700 | 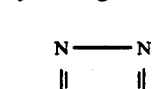 | — | 0 | OC$_3$H$_7$-$i$ | — |
| 701 | 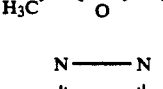 | — | 0 | SC$_2$H$_5$ | — |
| 702 | 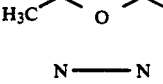 | CH$_2$ | 1 | CO$_2$CH$_3$ | — |
| 703 | 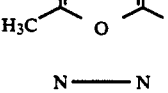 | — | 0 | SO$_2$C$_2$H$_5$ | — |
| 704 | 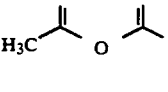 | — | 0 | OCF$_3$ | — |
| 705 | 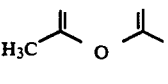 | — | 0 | C$_6$H$_5$ | — |
| 706 | 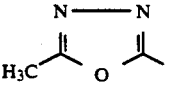 | — | 0 | CO$_2$C$_3$H$_7$ | — |
| 707 | 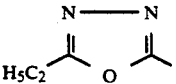 | — | 0 | OC$_2$H$_5$ | — |
| 708 | 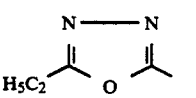 | — | 0 | SC$_3$H$_7$-$i$ | — |
| 709 | 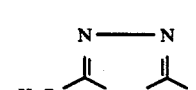 | — | 0 | SO$_2$N(CH$_3$)$_2$ | — |
| 710 | 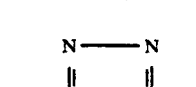 | — | 0 | CO$_2$CH$_3$ | — |
| 711 | 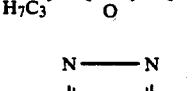 | — | 0 | SC$_2$H$_5$ | — |

| | | | | | |
|---|---|---|---|---|---|
| 712 | 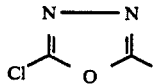 | — | 0 | CO$_2$CH$_3$ | — |
| 713 | 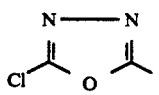 | — | 0 | Br | — |
| 714 | 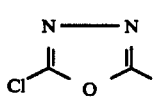 | — | 0 | OC$_2$H$_5$ | — |
| 715 | 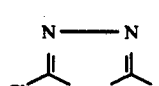 | — | 0 | SC$_2$H$_5$ | — |
| 716 | 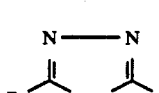 | — | 0 | CO$_2$CH$_3$ | (5)-Cl |
| 717 | 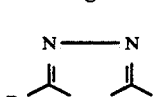 | — | 0 | Cl | — |
| 718 | 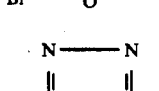 | — | 0 | OCF$_3$ | — |
| 719 | 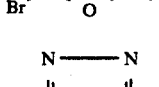 | — | 0 | C$_6$H$_5$ | — |
| 720 | 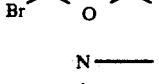 | — | 0 | CO$_2$CH$_3$ | — |
| 721 | 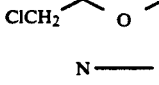 | — | 0 | SO$_2$C$_2$H$_5$ | — |
| 722 | 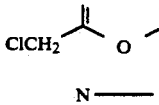 | — | 0 | CO$_2$CH$_3$ | — |
| 723 | 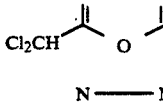 | — | 0 | OCF$_3$ | — |
| 724 | 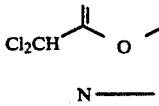 | — | 0 | CO$_2$CH$_3$ | — |
| 725 | 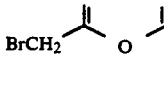 | — | 0 | SO$_2$C$_2$H$_5$ | — |
| 726 | 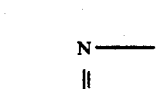 | — | 0 | CO$_2$C$_2$H$_5$ | — |

| | | | | | |
|---|---|---|---|---|---|
| 727 | N=N, H5C6–C(=)–O–C(=)–CH3 (with N—N) | — | 0 | OC2H5 | — |
| 728 | N=N, H5C6–C(=)–O–C(=)–CH3 | — | 0 | CO2CH3 | (5)-Cl |
| 729 | N=N, H5C6–C(=)–O–C(=)–CH3 | — | 0 | SO2N(CH3)(OCH3) | — |
| 730 | N=N, H5C6–C(=)–O–C(=)–CH3 | CH2 | 1 | CO2CH3 | — |
| 731 | N=N, H5C6–C(=)–O–C(=)–CH3 | — | 0 | Cl | — |
| 732 | N=N, H3CO–C(=)–O–C(=)–CH3 | — | 0 | CO2CH3 | — |
| 733 | N=N, H3CO–C(=)–O–C(=)–CH3 | — | 0 | C6H5 | — |
| 734 | N=N, H5C2O–C(=)–O–C(=)–CH3 | — | 0 | Br | — |
| 735 | N=N, i-H7C3O–C(=)–O–C(=)–CH3 | — | 0 | OCH3 | — |
| 736 | N=N, H3CS–C(=)–O–C(=)–CH3 | — | 0 | OCF3 | — |
| 737 | N=N, H3CS–C(=)–O–C(=)–CH3 | — | 0 | Cl | (6)-Cl |
| 738 | N=N, H5C2SO–C(=)–O–C(=)–CH3 | — | 0 | CF3 | — |
| 739 | N=N, H5C2SO2–C(=)–O–C(=)–CH3 | — | 0 | CO2CH3 | — |
| 740 | N=N, H5C2SO2–C(=)–O–C(=)–CH3 | — | 0 | OC2H5 | — |
| 741 | N=N, (H3C)2N–C(=)–O–C(=)–CH3 | — | 0 | SO2C3H7–i | — |

| No. | Het | — | n | R | X |
|---|---|---|---|---|---|
| 742 | thiadiazole (N=N, S, CH) | — | 0 | CO$_2$CH$_3$ | — |
| 743 | thiadiazole | — | 0 | CO$_2$CH$_3$ | (5)-Cl |
| 744 | thiadiazole | — | 0 | CO$_2$CH$_3$ | (6)-Cl |
| 745 | thiadiazole | — | 0 | OC$_2$H$_5$ | — |
| 746 | thiadiazole | — | 0 | SC$_2$H$_5$ | — |
| 747 | thiadiazole | — | 0 | SOC$_3$H$_{7-n}$ | — |
| 748 | thiadiazole | — | 0 | SO$_2$C$_2$H$_5$ | — |
| 749 | thiadiazole | — | 0 | Cl | — |
| 750 | thiadiazole | — | 0 | OCF$_3$ | — |
| 751 | thiadiazole | — | 0 | OCHF$_2$ | — |
| 752 | thiadiazole | — | 0 | CF$_3$ | — |
| 753 | thiadiazole | — | 0 | Cl | (6)-Cl |
| 754 | thiadiazole | — | 0 | CH$_3$ | — |
| 755 | dimethyl-thiadiazole | — | 0 | CO$_2$CH$_3$ | (5)-Cl |
| 756 | dimethyl-thiadiazole | — | 0 | Cl | — |

| | | | | | |
|---|---|---|---|---|---|
| 757 | 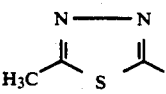 | — | 0 | OCF$_3$ | — |
| 758 | 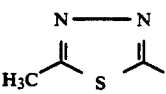 | — | 0 | OCHF$_2$ | — |
| 759 | 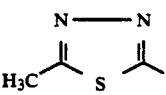 | — | 0 | OC$_2$H$_5$ | — |
| 760 | 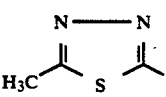 | — | 0 | SC$_2$H$_5$ | — |
| 761 | 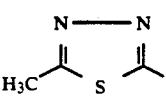 | — | 0 | SOC$_2$H$_5$ | — |
| 762 | 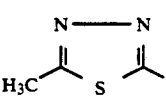 | — | 0 | SO$_2$C$_2$H$_5$ | — |
| 763 | 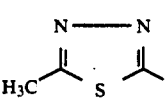 | — | 0 | C$_6$H$_5$ | — |
| 764 | 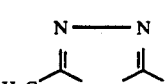 | — | 0 | Cl | (6)-CH$_3$ |
| 765 | 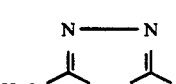 | — | 0 | Cl | — |
| 766 | 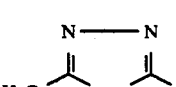 | — | 0 | CO$_2$CH$_3$ | — |
| 767 | 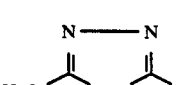 | — | 0 | CO$_2$C$_2$H$_5$ | — |
| 768 | 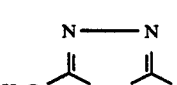 | — | 0 | SCH$_3$ | — |
| 769 | 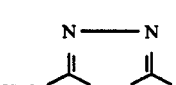 | — | 0 | SC$_2$H$_5$ | — |
| 770 | 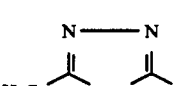 | — | 0 | OC$_2$H$_5$ | — |
| 771 | 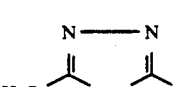 | — | 0 | SO$_2$C$_2$H$_5$ | — |

-continued

| # | Structure | | | | |
|---|---|---|---|---|---|
| 772 | 1,3,4-thiadiazole with n-H7C3 and CH3 | — | 0 | CO2CH3 | — |
| 773 | 1,3,4-thiadiazole with i-H7C3 and CH3 | — | 0 | CO2CH3 | — |
| 774 | 1,3,4-thiadiazole with i-H7C3 and CH3 | — | 0 | OC2H5 | — |
| 775 | 1,3,4-thiadiazole with Cl and CH3 | — | 0 | CO2CH3 | — |
| 776 | 1,3,4-thiadiazole with Cl and CH3 | — | 0 | OCH3 | — |
| 777 | 1,3,4-thiadiazole with Cl and CH3 | — | 0 | CO2CH3 | (5)-Cl |
| 778 | 1,3,4-thiadiazole with Cl and CH3 | — | 0 | CO2CH3 | (6)-Cl |
| 779 | 1,3,4-thiadiazole with Br and CH3 | — | 0 | CO2CH3 | — |
| 780 | 1,3,4-thiadiazole with Br and CH3 | — | 0 | SC2H5 | — |
| 781 | 1,3,4-thiadiazole with Br and CH3 | — | 0 | C6H5 | — |
| 782 | 1,3,4-thiadiazole with ClCH2 and CH3 | — | 0 | CO2CH3 | — |
| 783 | 1,3,4-thiadiazole with ClCH2 and CH3 | — | 0 | OC2H5 | — |
| 784 | 1,3,4-thiadiazole with ClCH2 and CH3 | — | 0 | OCF3 | — |
| 785 | 1,3,4-thiadiazole with Cl2CH and CH3 | — | 0 | CO2CH3 | — |
| 786 | 1,3,4-thiadiazole with Cl2CH and CH3 | — | 0 | C6H5 | — |

-continued

| No. | Structure | | R | | Sub |
|---|---|---|---|---|---|
| 787 | Br₂CH-C(=N-N=)S-C(CH₃) | — | 0 | CO₂CH₃ | — |
| 788 | Br₂CH-C(=N-N=)S-C(CH₃) | — | 0 | CO₂C₂H₅ | — |
| 789 | Br₂CH-C(=N-N=)S-C(CH₃) | — | 0 | CO₂CH₃ | — |
| 790 | Cl₃C-C(=N-N=)S-C(CH₃) | — | 0 | CO₂CH₃ | — |
| 791 | F₃C-C(=N-N=)S-C(CH₃) | — | 0 | CO₂CH₃ | — |
| 792 | H₅C₆-C(=N-N=)S-C(CH₃) | — | 0 | CO₂CH₃ | — |
| 793 | H₅C₆-C(=N-N=)S-C(CH₃) | — | 0 | CO₂C₂H₅ | — |
| 794 | H₅C₆-C(=N-N=)S-C(CH₃) | — | 0 | Cl | — |
| 795 | H₅C₆-C(=N-N=)S-C(CH₃) | — | 0 | OCF₃ | — |
| 796 | H₅C₆-C(=N-N=)S-C(CH₃) | — | 0 | OCH₃ | — |
| 797 | H₅C₆-C(=N-N=)S-C(CH₃) | — | 0 | OC₂H₅ | — |
| 798 | H₅C₆-C(=N-N=)S-C(CH₃) | — | 0 | SC₂H₅ | — |
| 799 | H₅C₆-C(=N-N=)S-C(CH₃) | — | 0 | SO₂C₃H₇-n | — |
| 800 | H₅C₆-C(=N-N=)S-C(CH₃) | — | 0 | CO₂CH₃ | (6)-Cl |
| 801 | H₅C₆-C(=N-N=)S-C(CH₃) | — | 0 | C₆H₅ | — |

-continued

| No. | Structure | | n | R | |
|---|---|---|---|---|---|
| 802 | H3CS-C(=N-N=C(CH3))-S (thiadiazole with SCH3 and CH3) | — | 0 | CO2CH3 | — |
| 803 | H3CS-...thiadiazole...CH3 | — | 0 | SO2N(CH3)2 | — |
| 804 | H3CS-...thiadiazole...CH3 | — | 0 | SC2H5 | — |
| 805 | H3CS-...thiadiazole...CH3 | — | 0 | C6H5 | — |
| 806 | H5C2S-...thiadiazole...CH3 | — | 0 | CO2CH3 | — |
| 807 | H7C3S-...thiadiazole...CH3 | — | 0 | CO2CH3 | — |
| 808 | i-H7C3S-...thiadiazole...CH3 | — | 0 | CO2CH3 | — |
| 809 | H5C2SO-...thiadiazole...CH3 | — | 0 | CO2C2H5 | — |
| 810 | H3CSO2-...thiadiazole...CH3 | — | 0 | CO2CH3 | — |
| 811 | H3CSO2-...thiadiazole...CH3 | — | 0 | OC2H5 | — |
| 812 | H3CSO2-...thiadiazole...CH3 | CH2 | 1 | CO2CH3 | — |
| 813 | H3CSO2-...thiadiazole...CH3 | — | 0 | OCF3 | — |
| 814 | H3CSO2-...thiadiazole...CH3 | — | 0 | C6H5 | — |
| 815 | (H3C)2N-...thiadiazole...CH3 | — | 0 | CO2CH3 | — |
| 816 | (H3C)2N-...thiadiazole...CH3 | — | 0 | CO2C2H5 | — |

-continued

| # | Structure | | | | |
|---|---|---|---|---|---|
| 817 | (CH₃)₂N-C(=N-N=C(CH₃)-S-)  [dimethylamino thiadiazole with methyl] | — | 0 | OC₂H₅ | — |
| 818 | (CH₃)₂N-C(=N-N=C(CH₃)-S-) | — | 0 | SC₂H₅ | — |
| 819 | (CH₃)₂N-C(=N-N=C(CH₃)-S-) | — | 0 | SO₂C₃H₇ | — |
| 820 | (CH₃)(C₂H₅)N-C(=N-N=C(CH₃)-S-) | — | 0 | CO₂CH₃ | — |
| 821 | (CH₃)(n-C₄H₉)N-C(=N-N=C(CH₃)-S-) | — | 0 | CO₂CH₃ | — |
| 822 | H₃CO-C(=N-N=C(CH₃)-S-) | — | 0 | CO₂CH₃ | — |
| 823 | H₃CO-C(=N-N=C(CH₃)-S-) | — | 0 | CO₂C₂H₅ | — |
| 824 | H₃CO-C(=N-N=C(CH₃)-S-) | — | 0 | OC₂H₅ | — |
| 825 | H₃CO-C(=N-N=C(CH₃)-S-) | — | 0 | SC₂H₅ | — |
| 826 | H₅C₂O-C(=N-N=C(CH₃)-S-) | — | 0 | CO₂CH₃ | — |
| 827 | H₅C₂O-C(=N-N=C(CH₃)-S-) | — | 0 | CO₂CH₃ | (5)-Cl |
| 828 | H₅C₂O-C(=N-N=C(CH₃)-S-) | — | 0 | OCF₃ | — |
| 829 | n-H₇C₃O-C(=N-N=C(CH₃)-S-) | — | 0 | CO₂CH₃ | — |
| 830 | i-H₇C₃O-C(=N-N=C(CH₃)-S-) | — | 0 | CO₂CH₃ | — |

-continued

| # | Structure | | | Substituent | |
|---|---|---|---|---|---|
| 831 | [1,3,4-thiadiazole with n-H9C4O and CH3] | — | 0 | CO2CH3 | — |
| 832 | [isoxazole with H3C] | — | 0 | CO2C2H5 | — |
| 833 | [isoxazole with H3C] | — | 0 | CO2CH3 | (5)-Cl |
| 834 | [isoxazole with H3C] | — | 0 | CO2CH3 | (6)-Cl |
| 835 | [isoxazole with H5C2] | — | 0 | CO2CH3 | — |
| 836 | [isoxazole with H5C2] | — | 0 | CO2C2H5 | — |
| 837 | [isoxazole with H5C2] | — | 0 | OCH3 | — |
| 838 | [isoxazole with H5C2] | — | 0 | OC2H5 | — |
| 839 | [isoxazole with H5C2] | — | 0 | SC2H5 | — |
| 840 | [isoxazole with H5C2] | — | 0 | SCH3 | — |
| 841 | [isoxazole with H5C2] | — | 0 | SO2CH3 | — |
| 842 | [isoxazole with H5C2] | — | 0 | SO2C2H5 | — |
| 843 | [isoxazole with H5C2] | — | 0 | OCF3 | — |
| 844 | [isoxazole with H5C2] | — | 0 | C6H5 | — |
| 845 | [isoxazole with H5C2] | — | 0 | Cl | (6)-CH3 |

-continued

| # | Structure | | | |
|---|---|---|---|---|
| 846 | isoxazole, H7C3- | — | 0 | CO2CH3 | — |
| 847 | isoxazole, H7C3- | — | 0 | OC2H5 | — |
| 848 | isoxazole, i-H7C3- | — | 0 | CO2CH3 | — |
| 849 | isoxazole, i-H7C3- | — | 0 | SO2CH3 | — |
| 850 | isoxazole, i-H7C3- | — | 0 | SO2N(CH3)2 | — |
| 851 | isoxazole, i-H7C3- | — | 0 | OCF3 | — |
| 852 | isoxazole, ClCH2- | — | 0 | CO2C2H5 | — |
| 853 | isoxazole, ClCH2- | — | 0 | OC2H5 | — |
| 854 | isoxazole, ClCH2- | — | 0 | SC2H5 | — |
| 855 | isoxazole, ClCH2- | — | 0 | SO2C2H5 | — |
| 856 | isoxazole, ClCH2- | — | 0 | C6H5 | — |
| 857 | isoxazole, Cl2CH- | — | 0 | CO2CH3 | — |
| 858 | isoxazole, Cl2CH- | — | 0 | CO2C2H5 | — |
| 859 | isoxazole, Cl2CH- | — | 0 | SO2C2H5 | — |
| 860 | isoxazole, Cl2CH- | — | 0 | OCH3 | — |

| | | | | | |
|---|---|---|---|---|---|
| 861 | isoxazole with Cl₂CH | — | 0 | OC₂H₅ | — |
| 862 | isoxazole with BrCH₂ | — | 0 | CO₂CH₃ | — |
| 863 | isoxazole with BrCH₂ | — | 0 | CO₂C₂H₅ | — |
| 864 | isoxazole with BrCH₂ | — | 0 | Cl | — |
| 865 | isoxazole with BrCH₂ | — | 0 | OC₂H₅ | — |
| 866 | isoxazole with Br₂CH | — | 0 | CO₂CH₃ | — |
| 867 | isoxazole with Br₂CH | — | 0 | SO₂C₂H₅ | — |
| 868 | isoxazole with F₂CH | — | 0 | CO₂CH₃ | — |
| 869 | isoxazole with F₂CH | — | 0 | C₆H₅ | — |
| 870 | isoxazole with F₃C | — | 0 | CO₂CH₃ | — |
| 871 | isoxazole with F₃C | — | 0 | OC₂H₅ | — |
| 872 | isoxazole with H₃C, CH₃ | — | 0 | CO₂CH₃ | — |
| 873 | isoxazole with H₃C, CH₃ | — | 0 | CO₂C₂H₅ | — |
| 874 | isoxazole with H₃C, CH₃ | — | 0 | Cl | — |

| # | Structure | | | R | Position |
|---|---|---|---|---|---|
| 875 | 4,5-dimethylisoxazol-3-yl | — | 0 | Cl | (6)-Cl |
| 876 | 5-methyl-4-methylisoxazol-3-yl | — | 0 | OCH₃ | — |
| 877 | 5-methyl-4-methylisoxazol-3-yl | — | 0 | OC₂H₅ | — |
| 878 | 5-methyl-4-methylisoxazol-3-yl | — | 0 | SC₂H₅ | — |
| 879 | 5-methyl-4-methylisoxazol-3-yl | — | 0 | SO₂C₂H₅ | — |
| 880 | 5-methyl-4-methylisoxazol-3-yl | — | 0 | C₆H₅ | — |
| 881 | 5-methyl-4-methylisoxazol-3-yl | — | 0 | OCF₃ | — |
| 882 | 5-methyl-4-ethylisoxazol-3-yl | — | 0 | CO₂CH₃ | — |
| 883 | 5-methyl-4-ethylisoxazol-3-yl | — | 0 | CO₂C₂H₅ | — |
| 884 | 5-methyl-4-n-propylisoxazol-3-yl | — | 0 | CF₃ | — |
| 885 | 5-ethyl-4-methylisoxazol-3-yl | — | 0 | SO₂N(CH₃)₂ | — |
| 886 | 5-ethyl-4-methylisoxazol-3-yl | — | 0 | OCF₃ | — |

-continued

| # | Structure | | | |
|---|---|---|---|---|
| 887 | 3-methyl-4-methyl-5-isopropyl-isoxazol-yl | — | 0 | OCH$_3$ | — |
| 888 | 4-methoxy-3-methyl-isoxazol-yl | — | 0 | OC$_2$H$_5$ | — |
| 889 | 4-methoxy-3-methyl-isoxazol-yl | — | 0 | CO$_2$CH$_3$ | — |
| 890 | 3-methyl-4-methoxy-5-methyl-isoxazol-yl | — | 0 | SO$_2$C$_2$H$_5$ | — |
| 891 | 3-methyl-4-methoxy-5-ethyl-isoxazol-yl | — | 0 | CO$_2$CH$_3$ | — |
| 892 | 4-methyl-isoxazol-yl | — | 0 | CO$_2$CH$_3$ | — |
| 893 | 4-methyl-isoxazol-yl | — | 0 | Br | — |
| 894 | 4-methyl-isoxazol-yl | — | 0 | OC$_2$H$_5$ | — |
| 895 | 4-ethyl-isoxazol-yl | — | 0 | CO$_2$CH$_3$ | — |
| 896 | 4-ethyl-isoxazol-yl | — | 0 | OCF$_3$ | — |
| 897 | 4-propyl-isoxazol-yl | — | 0 | SO$_2$C$_2$H$_5$ | — |
| 898 | 4-propyl-isoxazol-yl | — | 0 | CO$_2$CH$_3$ | — |

| | | | | | |
|---|---|---|---|---|---|
| 899 | isoxazole-Ph | — | 0 | CO$_2$CH$_3$ | — |
| 900 | isoxazole-Ph | — | 0 | CO$_2$C$_2$H$_5$ | — |
| 901 | isoxazole-Ph | — | 0 | SC$_2$H$_5$ | — |
| 902 | isoxazole | — | 0 | CO$_2$C$_2$H$_5$ | — |
| 903 | isoxazole | — | 0 | CO$_2$CH$_3$ | (5)-Cl |
| 904 | isoxazole | — | 0 | CO$_2$CH$_3$ | (6)-Cl |
| 905 | isoxazole | — | 0 | F | — |
| 906 | isoxazole | — | 0 | Cl | — |
| 907 | isoxazole | — | 0 | OCH$_3$ | — |
| 908 | isoxazole | — | 0 | OC$_2$H$_5$ | — |
| 909 | isoxazole | — | 0 | SC$_2$H$_5$ | — |
| 910 | isoxazole | — | 0 | SO$_2$C$_3$H$_7$ | — |
| 911 | isoxazole | — | 0 | C$_6$H$_5$ | — |
| 912 | isoxazole (N—O) | — | 0 | CO$_2$C$_2$H$_5$ | — |
| 913 | isoxazole (N—O) | — | 0 | CO$_2$CH$_3$ | (5)-Cl |

| 914 | 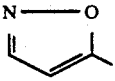 | — | 0 | CO₂CH₃ | (6)-Cl |
| 915 | 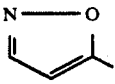 | — | 0 | OCF₃ | — |
| 916 | 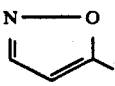 | — | 0 | Cl | — |
| 917 | 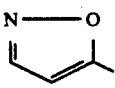 | — | 0 | OC₂H₅ | — |
| 918 | 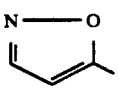 | — | 0 | SCH₃ | — |
| 919 | 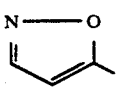 | — | 0 | SO₂C₂H₅ | — |
| 920 | 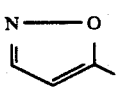 | — | 0 | C₆H₅ | — |
| 921 | 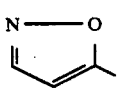 | — | 0 | OCHF₂ | — |
| 922 | 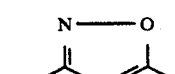 | — | 0 | CO₂C₂H₅ | — |
| 923 | 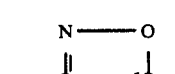 | — | 0 | Cl | — |
| 924 | 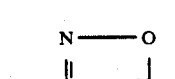 | — | 0 | OCH₃ | — |
| 925 | 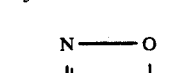 | — | 0 | OC₂H₅ | — |
| 926 | 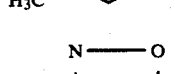 | — | 0 | CO₂CH₃ | — |
| 927 | 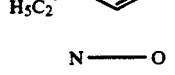 | — | 0 | OCF₃ | — |
| 928 | 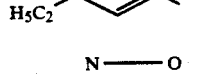 | — | 0 | SO₂N(CH₃)₂ | — |
| 929 | 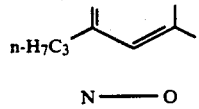 | — | 0 | C₆H₅ | — |

| # | Structure | | | |
|---|---|---|---|---|
| 930 | isoxazole with t-H9C4 and CH3 | — | 0 | CO2CH3 | — |
| 931 | isoxazole with H5C6 and CH3 | — | 0 | CO2CH3 | — |
| 932 | isoxazole with H3C, CH3, CH3 | — | 0 | CO2CH3 | — |
| 933 | isoxazole with H3C, CH3, CH3 | CH2 | 1 | CO2CH3 | — |
| 934 | isoxazole with H3C, CH3, CH3 | — | 0 | OCHF2 | — |
| 935 | isoxazole with H3C, CH3, CH3 | — | 0 | C6H5 | — |
| 936 | isoxazole with H3C, C2H5, CH3 | — | 0 | CO2CH3 | — |
| 937 | isoxazole with H3C, C2H5, CH3 | — | 0 | OC2H5 | — |
| 938 | isoxazole with H5C2, CH3, CH3 | — | 0 | CO2CH3 | — |
| 939 | isoxazole with H5C6, CH3, CH3 | — | 0 | CO2CH3 | — |
| 940 | isoxazole with F3C, CH3, CH3 | — | 0 | SO2C2H5 | — |
| 941 | isoxazole with Cl, Cl, CH3 | — | 0 | CO2CH3 | — |

-continued

| # | Structure | | | |
|---|---|---|---|---|
| 942 | isoxazole | — | 0 CO₂CH₃ | — |
| 943 | isoxazole | — | 0 CO₂CH₃ | (5)-Cl |
| 944 | isoxazole | — | 0 CO₂C₂H₅ | — |
| 945 | isoxazole | — | 0 OCH₃ | — |
| 946 | isoxazole | — | 0 OC₂H₅ | — |
| 947 | isoxazole | — | 0 OCF₃ | — |
| 948 | isoxazole | — | 0 Cl | — |
| 949 | isoxazole | — | 0 SC₂H₅ | — |
| 950 | isoxazole | — | 0 SO₂C₂H₅ | — |
| 951 | isoxazole | — | 0 C₃H₇ | — |
| 952 | isoxazole-CH₃ | — | 0 CO₂CH₃ | — |
| 953 | isoxazole-CH₃ | — | 0 CO₂C₂H₅ | — |
| 954 | isoxazole-CH₃ | — | 0 SC₂H₅ | — |
| 955 | isoxazole-CH₃ | — | 0 OC₂H₅ | — |
| 956 | isoxazole-C₂H₅ | — | 0 CO₂CH₃ | — |
| 957 | isoxazole-C₃H₇ | — | 0 CO₂CH₃ | — |

| No. | Structure | | | | |
|---|---|---|---|---|---|
| 958 | N=/−C₆H₅ with CH₃, O on N | — | 0 | CO₂CH₃ | — |
| 959 | N=/ with CH₃, CH₃, O on N | — | 0 | CO₂CH₃ | — |
| 960 | N=/ with CH₃, CH₃, O on N | — | 0 | CO₂CH₃ | (5)-Cl |
| 961 | N=/ with CH₃, CH₃, O on N | — | 0 | CO₂CH₃ | (6)-Cl |
| 962 | N=/ with CH₃, CH₃, O on N | — | 0 | OCH₃ | — |
| 963 | N=/ with CH₃, CH₃, O on N | — | 0 | OC₂H₅ | — |
| 964 | N=/ with CH₃, C₆H₅, O on N | — | 0 | CO₂CH₃ | — |
| 965 | N=/ with CH₃, CH₂Cl, O on N | — | 0 | CO₂CH₃ | — |
| 966 | N=/ with CH₃, CF₃, O on N | — | 0 | CO₂CH₃ | — |
| 967 | N=/ with CH₃, CH₃, CH₃, O on N | — | 0 | CO₂C₂H₅ | — |
| 967 | N=/ with CH₃, CH₃, CH₃, O on N | — | 0 | CO₂CH₃ | (6)-Cl |
| 968 | N=/ with CH₃, CH₃, CH₃, O on N | — | 0 | OCF₃ | — |

| No. | R | | | |
|---|---|---|---|---|
| 969 | isoxazoline with CH₃, CH₃ (on ring C=N−O) | — | 0 | OC₂H₅ | — |
| 971 | isoxazoline with CH₃, CH₃ | — | 0 | SC₃H₇−i | — |
| 972 | isoxazoline with CH₃, CH₃ | — | 0 | SO₂C₂H₅ | — |
| 973 | isoxazoline with CH₃, CH₃ | — | 0 | SO₂C₃H₇−i | — |
| 974 | isoxazoline with CH₃, C₂H₅ | — | 0 | CO₂CH₃ | — |
| 975 | isoxazoline with CH₃, C₂H₅ | — | 0 | OCH₃ | — |
| 976 | isoxazoline with CH₃, C₃H₇−i | — | 0 | OC₂H₅ | — |
| 977 | isoxazoline with C₂H₅, CH₃ | — | 0 | CO₂CH₃ | — |
| 978 | isoxazoline with C₃H₇−n, CH₃ | — | 0 | OCF₃ | — |
| 979 | isoxazoline with C₆H₅, CH₃ | — | 0 | SO₂N(CH₃)₂ | — |
| 980 | isoxazoline with CH₃, C₆H₅ | — | 0 | CO₂CH₃ | — |

| | | | | | |
|---|---|---|---|---|---|
| 981 | isoxazole with C2H5, CH3, C6H5 substituents | — | 0 | CO2CH3 | — |
| 982 | isothiazole | — | 0 | CO2CH3 | — |
| 983 | isothiazole | — | 0 | CO2C2H5 | — |
| 984 | isothiazole | — | 0 | CO2CH3 | (5)-Cl |
| 985 | isothiazole | — | 0 | Cl | (6)-Cl |
| 986 | isothiazole | — | 0 | OCH3 | — |
| 987 | isothiazole | — | 0 | OC2H5 | — |
| 988 | isothiazole | — | 0 | OCF3 | — |
| 989 | isothiazole | — | 0 | SC2H5 | — |
| 990 | isothiazole | — | 0 | SO2C2H5 | — |
| 991 | isothiazole | — | 0 | C6H5 | — |
| 992 | isothiazole-CH3 | — | 0 | CO2CH3 | — |
| 993 | isothiazole-CH3 | — | 0 | CO2C2H5 | — |
| 994 | isothiazole-CH3 | — | 0 | OC2H5 | — |
| 995 | isothiazole-CH3 | — | 0 | SC2H5 | — |
| 996 | isothiazole-C2H5 | — | 0 | CO2CH3 | — |

| No. | Structure | A | n | R | — |
|---|---|---|---|---|---|
| 997 | S—N, H5C2, (ring) | — | 0 | CO2C2H5 | — |
| 998 | S—N, H5C2, (ring) | — | 0 | OCH3 | — |
| 999 | S—N, H5C2, (ring) | — | 0 | SCH3 | — |
| 1000 | S—N, H5C2, (ring) | — | 0 | SC2H5 | — |
| 1001 | S—N, H5C2, (ring) | — | 0 | OCF3 | — |
| 1002 | S—N, H5C2, (ring) | — | 0 | SO2C2H5 | — |
| 1003 | S—N, H5C2, (ring) | — | 0 | C6H5 | — |
| 1004 | S—N, H5C2, (ring) | CH2 | 1 | CO2CH3 | — |
| 1005 | S—N, n-H7C3, (ring) | — | 0 | CO2CH3 | — |
| 1006 | S—N, i-H7C3, (ring) | — | 0 | CO2CH3 | — |
| 1007 | S—N, H5C6, (ring) | — | 0 | CO2CH3 | — |
| 1008 | S—N, ClCH2, (ring) | — | 0 | CO2CH3 | — |
| 1009 | S—N, ClCH2, (ring) | — | 0 | OC2H5 | — |
| 1010 | S—N, Cl2CH, (ring) | — | 0 | CO2CH3 | — |
| 1011 | S—N, F3C, (ring) | — | 0 | CO2CH3 | — |

| No. | Structure | Linker | n | R | — |
|---|---|---|---|---|---|
| 1012 | isothiazole, 4,5-diCH₃ | — | 0 | CO₂CH₃ | — |
| 1013 | isothiazole, 4,5-diCH₃ | CH₂ | 1 | CO₂CH₃ | — |
| 1014 | isothiazole, 4,5-diCH₃ | — | 0 | Cl | — |
| 1015 | isothiazole, 5-CH₃, 4-C₂H₅ | — | 0 | CO₂CH₃ | — |
| 1016 | isothiazole, 5-CH₃, 4-C₃H₇ | — | 0 | SCH₃ | — |
| 1017 | isothiazole, 5-C₂H₅, 4-CH₃ | — | 0 | SO₂C₂H₅ | — |
| 1018 | isothiazole, 5-C₆H₅, 4-CH₃ | — | 0 | CO₂CH₃ | — |
| 1019 | isothiazole, 5-CH₃, 4-C₆H₅ | — | 0 | CO₂CH₃ | — |
| 1020 | isothiazole, 5-i-C₃H₇, 4-CH₃ | — | 0 | OCF₃ | — |
| 1021 | isothiazole, 5-C₂H₅, 4-C₂H₅ | — | 0 | OC₂H₅ | — |
| 1022 | isothiazole (N—S, 3-CH₃) | — | 0 | CO₂CH₃ | — |
| 1023 | isothiazole (N—S, 3,5-diCH₃) | — | 0 | CO₂C₂H₅ | — |

| # | Structure | | | |
|---|---|---|---|---|
| 1024 | isothiazole with 3-CH₃, 5-CH₃ | — | 0 CO₂CH₃ | — |
| 1025 | isothiazole with 3-CH₃, 4-CH₃, 5-CH₃ | — | 0 CO₂CH₃ | — |
| 1026 | isothiazole with 3-C₂H₅, 4-CH₃, 5-CH₃ | — | 0 C₆H₅ | — |
| 1027 | isothiazole with 4-CH₃, 5-CH₃ | — | 0 CO₂CH₃ | — |
| 1028 | isothiazole with 4-CH₂Cl, 5-CH₃ | — | 0 CO₂CH₃ | — |
| 1029 | isothiazole with 3-C₆H₅, 5-CH₃ | — | 0 OC₂H₅ | — |
| 1030 | isothiazole with 4-C₆H₅ | — | 0 CO₂C₂H₅ | — |
| 1031 | isothiazole with 3-Cl, 4-Cl, 5-CH₃ | — | 0 CO₂CH₃ | — |
| 1032 | thiazole | — | 0 CO₂CH₃ | — |
| 1033 | thiazole with 4-CH₃ | — | 0 CO₂CH₃ | — |
| 1034 | thiazole with 4-CH₃ | — | 0 OCF₃ | — |
| 1035 | thiazole with 4-CH₃, 5-CH₃ | — | 0 CO₂CH₃ | — |
| 1036 | thiazole with 4-CH₃, 5-CH₃ | — | 0 CO₂C₂H₅ | — |

| | | | | | |
|---|---|---|---|---|---|
| 1037 | N=C(CH₃)-C(C₂H₅)=... (N-S ring with CH₃ and C₂H₅) | — | 0 | OC₂H₅ | — |
| 1038 | N=CH-C(CH₃)=... (N-S ring with CH₃) | — | 0 | CO₂CH₃ | — |
| 1039 | N=CH-C(C₆H₅)=... (N-S ring with C₆H₅) | — | 0 | CO₂C₂H₅ | — |
| 1040 | N=C(C₆H₅)-C(CH₃)=... (N-S ring with C₆H₅ and CH₃) | — | 0 | SO₂C₂H₅ | — |
| 1041 | N=C(CH₃)-C(C₃H₇-n)=... (N-S ring with CH₃ and n-C₃H₇) | — | 0 | CO₂CH₃ | — |

USE EXAMPLES

EXAMPLE A

Pre-emergence test

Solvent: 5 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, the compound according to Preparation Example 1 exhibits a very good herbicidal activity combined with good tolerability by the productive plants.

EXAMPLE B

Post-emergence test

Solvent: 5 parts by weight of acetone
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 1,000 l of water/ha. After three weeks, the degree of damage to the plants is rated in % damage in comparison to the development of the untreated control. The figures denote:

0% = no action (like untreated control)
100% = total destruction

In this test, the compound according to Preparation Example 1 exhibits a very good herbicidal action combined with excellent cultivated plant selectivity.

It will be understood that the specification and examples are illustrative but not limitative of the present invention and that other embodiments within the spirit and scope of the invention will suggest themselves to those skilled in the art.

We claim:

1. A sulphonylated carboxamide of the formula $$R^1—CO—NH—SO_2—(A)_n—R^2 \quad (I)$$

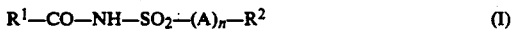

in which n represents the number 0 or 1,

A represents oxygen, imino (NH) or methylene (CH₂), $R^1$ represents a five-membered heteroaryl radical from the group consisting of oxazolyl, isoxazolyl, thiazolyl, isothiazolyl, oxadiazolyl and thiadiazolyl, which is optionally monosubstituted or polysubstitututed by identical or different halogen or by optionally halogen-substituted $C_1$-$C_6$-alkyl, phenyl, $C_1-C_6$-alkoxy, $C_1-C_6$-alkylthio, $C_1-C_6$-alkylsulphinyl, $C_1-C_6$-alkylsulphonyl, $C_1-C_6$-alkylamino or di-($C_1-C_6$-alkyl)amino, and $R^2$ represents the radical

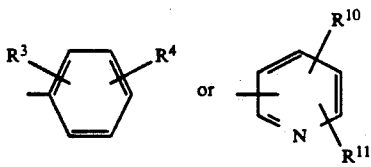

in which $R^3$ and $R^4$ are identical or different and represent hydrogen, fluorine, chlorine, bromine, iodine, cyano, nitro, carboxyl or $C_1-C_6$-alkyl which is optionally substituted by fluorine, chlorine, bromine, cyano, carboxyl, $C_1-C_4$-alkoxycarbonyl, $C_1-C_4$-alkylamino-carbonyl, di-($C_1-C_4$-alkyl)aminocarbonyl, hydroxyl, $C_1-C_4$-alkoxy, formyloxy, $C_1-C_4$-alkyl-carbonyloxy, $C_1-C_4$-alkoxycarbonyloxy, $C_1-C_4$-alkylamino-carbonyloxy, $C_1-C_4$-alkylthio, $C_1-C_4$-alkylsulphinyl, $C_1-C_4$-alkylsulphonyl, di-($C_1-C_4$-alkyl)aminosulphonyl, $C_3-C_6$-cycloalkyl or phenyl, or $R^3$ and $R^4$ furthermore independently of one another represent $C_2-C_6$-alkenyl which is optionally substituted by fluorine, chlorine, bromine, cyano, $C_1-C_4$-alkoxycarbonyl, carboxyl or phenyl, or $R^3$ and $R^4$ additionally independently of one another represent $C_2-C_6$-alkinyl which is optionally substituted by fluorine, chlorine, bromine, cyano, $C_1-C_4$-alkoxy-carbonyl, carboxyl or phenyl; $C_1-C_4$-alkoxy which is optionally substituted by fluorine, chlorine, bromine, cyano, carboxyl, $C_1-C_4$-alkoxyacarbonyl, $C_1-C_4$-alkoxy, $C_1-C_4$-alkylthio, $C_1-C_4$-alkylsulphinyl or $C_1-C_4$-alkylsulphonyl; $C_1-C_4$-alkylthio which is optionally substituted by fluorine, chlorine, bromine, cyano, carboxyl, $C_1-C_4$-alkoxycarbonyl, $C_1-C_4$-alkylthio, $C_1-C_4$-alkylsulphinyl or $C_1-C_4$-alkylsulphonyl; $C_3-C_6$-alkenyloxy which is optionally substituted by fluorine, chlorine, bromine, cyano or $C_1-C_4$-alkoxy-carbonyl, $C_2-C_6$-alkenylthio which is optionally substituted by fluorine, chlorine, bromine, cyano, nitro, $C_1-C_3$-alkylthio or $C_1-C_4$-alkoxy-carbonyl; $C_3-C_6$-alkynyloxy, $C_3-C_6$-alkylthio or the radical $-S(O)_p-R^5$, or $R^3$ and $R^4$ furthermore represent phenyl or phenoxy, $C_1-C_4$-alkylcarbonylamino, $C_1-C_4$-alkoxycarbonylamino, $C_1-C_4$-alkylamino-carbonylamino, di-($C_1-C_4$-alkyl)-amino-carbonylamino, or the radical $-CO-R^6$, or $R^3$ and $R^4$ furthermore represent $C_1-C_4$-alkylsulphonyloxy, di-($C_1-C_4$-alkyl)-aminosulphonylamino or the radical $-CH=N-R^7$, in which p represents the numbers 1 or 2 and $R^5$ represents $C_1-C_4$-alkyl which is optionally substituted by fluorine, chlorine, bromine, cyano or $C_1-C_4$-alkoxycarbonyl, or $R^5$ represents $C_1-C_4$-alkoxy, $C_1-C_4$-alkoxy-$C_1-C_4$-alkylamino or di-($C_1-C_4$-alkyl)-amino, $R^6$ represents $C_1-C_6$-alkyl, $C_1-C_6$-alkoxy which is optionally substituted by fluorine, chlorine, methoxy or ethoxy; $C_3-C_6$-cycloalkoxy, $C_3-C_6$-alkenyloxy, $C_1-C_4$-alkylthio, amino, $C_1-C_4$-alkylamino, $C_1-C_4$-alkoxyamino, $C_1-C_4$-alkoxy-$C_1-C_4$-alkyl-amino or di-($C_1-C_4$-alkyl)amino which are optionally substituted by fluorine or chlorine and $R^7$ represents $C_1-C_6$-alkyl which is optionally substituted by fluorine, chlorine, cyano, carboxyl, $C_1-C_4$-alkoxy, $C_1-C_4$-alkylthio, $C_1-C_4$-alkylsulphinyl or $C_1-C_4$-alkylsulphonyl, benzyl which is optionally substituted by fluorine or chlorine, $C_3-C_6$-alkenyl or $C_3-C_6$-alkynyl which are optionally substituted by fluorine or chlorine, phenyl which is optionally substituted by fluorine, chlorine, bromine, $C_1-C_4$-alkyl, $C_1-C_4$-alkoxy, trifluoromethyl, trifluoromethoxy or trifluoromethylthio, $C_1-C_6$-alkoxy, $C_3-C_6$-alkenyloxy, $C_3-C_6$-alkynyloxy or benzyloxy which are optionally substituted by fluorine or chlorine, or $R^7$ furthermore represents amino, $C_1-C_4$-alkylamino, di($C_1-C_4$-alkyl)-amino, phenylamino, $C_1-C_4$-alkyl-carbonylamino, $C_1-C_4$-alkoxycarbonylamino, $C_1-C_4$-alkyl-sulphonylamino or phenyl sulphonylamino which is optionally substituted by fluorine, chlorine, bromine or methyl, $R^{10}$ and $R^{11}$ are identical or different and represent hydrogen, fluorine, chlorine, bromine, nitro, cyano, or $C_1-C_4$-alkyl which is optionally substituted by fluorine or chlorine; $C_2-C_4$-alkenyl which is optionally substituted by fluorine or chlorine, $C_1-C_4$-alkoxy which is optionally substituted by fluorine or chlorine; $C_1-C_4$-alkylthio, $C_1-C_4$-alkylsulphinyl or $C_1-C_4$-alkylsulphonyl which are optionally substituted by fluorine or chlorine; and di-($C_1-C_4$-alkyl)-aminosulphonyl, $C_1-C_4$-alkoxycarbonyl, dimethylaminocarbonyl or dioxolanyl;

or a salt thereof, with the exclusion of the compound 2-(dimethylamino)-N-[(4-methylphenyl)sulphonyl]-5-thiazole carboxamide.

2. A sulphonylated carboxamide according to claim 1, in which n represents the numbers 0 or 1, A represents oxygen, imino (NH) or methylene ($CH_2$), $R^1$ represents a five-membered heteroaryl radical from the group consisting of oxazolyl, isoxazolyl, thiazolyl, 1,2,4-oxadiazolyl, 1,3,4-oxadiazolyl, 1,2,4-thiadiazolyl and 1,3,4-thiadiazolyl, which is optionally substituted by fluorine, chlorine, bromine, methyl, ethyl, propyl, isopropyl, butyl, isobutyl, sec-butyl, tert-butyl, fluoromethyl, chloromethyl, difluoromethyl, dichloromethyl, trifluoromethyl, trichloromethyl, chlorofluoromethyl, chlorodifluoromethyl, fluorodichloromethyl, phenyl, methoxy, ethoxy, propoxy, isopropyloxy, difluoromethoxy, trifluoromethoxy, chlorodifluoromethoxy, methylthio, ethylthio, propylthio, isopropylthio, difluoromethylthio, trifluoromethylthio, chlorodifluoromethylthio, methylsulphinyl, ethylsulphinyl, propylsulphinyl, methylsulphonyl, ethylsulphonyl, propylsulphonyl, methylamino, ethylamino, propylamino, isopropylamino or dimethylamino, and $R^2$ represents the radical

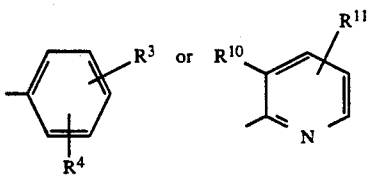

in which

R³ represents hydrogen, fluorine, chlorine, bromine, cyano, nitro, carboxyl, methyl, trifluoromethyl, methoxy, ethoxy, 2-chloroethoxy, difluoromethoxy, trifluoromethoxy, $C_1$–$C_3$-alkylthio, $C_1$–$C_3$-alkyl-sulphinyl, $C_1$–$C_3$-alkylsulphonyl, dimethylaminosulphonyl, diethylaminosulphonyl, N-methoxy-N-methylaminosulphonyl, phenyl, phenoxy or $C_1$–$C_3$-alkoxycarbonyl and R⁴ represents hydrogen, fluorine, chlorine, bromine, methyl, trifluoromethyl or methoxy, R¹⁰ represents dimethylaminocarbonyl or $C_1$–$C_4$-alkylsulphonyl, and R¹¹ represents hydrogen, fluorine or chlorine or a salt thereof, with the exclusion of the compound 2-(dimethylamino)-N-[(4-methylphenyl)-sulphonyl]-5-thiazole carboxamide.

3. A method of combating unwanted vegetation which comprises applying to such vegetation or to a locus from which is it desired to exclude such vegetation a herbicidally effective amount of a sulphonylated carboxamide of the formula $$R^1-CO-NH-SO_2-(A)_n-R^2 \quad (I)$$

in which n represents the numbers of 0 or 1,

A represents oxygen, imino (NH) or methylene ($CH_2$),

R¹ represents a five-membered heteroaryl radical from the group consisting of oxazolyl, isoxazolyl, thiazolyl, isothiazolyl, oxadiazolyl and thiadiazolyl, which is optionally monosubstituted or polysubstituted by identical to different halogen or by optionally halogen-substituted $C_1$–$C_6$-alkyl, phenyl, $C_1$–$C_6$-alkoxy, $C_1$–$C_6$-alkylthio, $C_1$–$C_6$-alkylsulphinyl, $C_1$–$C_6$-alkylsulphonyl, $C_1$–$C_6$-alkylamino or di-($C_1$–$C_4$-alkyl)amino, and R² represents the radical

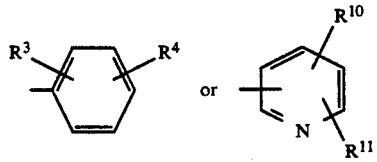

in which

R³ and R⁴ are identical or different and represent hydrogen, fluorine, chlorine, bromine, iodine, cyano, nitro, carboxyl or $C_1$–$C_6$-alkyl which is optionally substituted by fluorine, chlorine, bromine, cyano, carboxyl, $C_1$–$C_4$-alkoxycarbonyl, $C_1$–$C_4$-alkylamino-carbonyl, di-($C_1$–$C_4$-alkyl)aminocarbonyl, hydroxyl, $C_1$–$C_4$-alkoxy, formyloxy, $C_1$–$C_4$-alkyl-carbonyloxy, $C_1$–$C_4$-alkoxycarbonyloxy, $C_1$–$C_4$-alkylamino-carbonyloxy, $C_1$–$C_4$-alkylthio, $C_1$–$C_4$-alkylsulphinyl, $C_1$–$C_4$-alkylsulphonyl, di-($C_1$–$C_4$-alkyl)aminosulphonyl, $C_3$–$C_6$-cycloalkyl or phenyl, or R³ and R⁴ furthermore independently of one another represent $C_2$–$C_6$-alkenyl which is optionally substituted by fluorine, chlorine, bromine, cyano, $C_1$–$C_4$-alkoxycarbonyl, carboxyl or phenyl, or R³ and R⁴ additionally independently of one another represent $C_2$–$C_6$-alkinyl which is optionally substituted by fluorine, chlorine, bromine, cyano, $C_1$–$C_4$-alkoxy-carbonyl, carboxyl or phenyl; $C_1$–$C_4$-alkoxy which is optionally substituted by fluorine, chlorine, bromine, cyano, carboxyl, $C_1$–$C_4$-alkoxycarbonyl, $C_1$–$C_4$-alkoxy, $C_1$–$C_4$-alkylthio, $C_1$–$C_4$-alkylsulphinyl or $C_1$–$C_4$-alkylsulphonyl; $C_1$–$C_4$-alkylthio which is optionally substituted by fluorine, chlorine, bromine, cyano, carboxyl, $C_1$–$C_4$-alkoxycarbonyl, $C_1$–$C_4$-alkylthio, $C_1$–$C_4$-alkylsulphinyl or $C_1$–$C_4$-alkylsulphonyl; $C_3$–$C_6$-alkenyloxy which is optionally substituted by fluorine, chlorine, bromine, cyano or $C_1$–$C_4$-alkoxy-carbonyl, $C_2$–$C_6$-alkenylthio which is optionally substituted by fluorine, chlorine, bromine, cyano, nitro, $C_1$–$C_3$-alkylthio or $C_1$–$C_4$-alkoxy-carbonyl; $C_3$–$C_6$-alkynyloxy, $C_3$–$C_6$-alkynylthio or the radical $-S(O)_p-R^5$, or R³ and R⁴ furthermore represent phenyl or phenoxy, $C_1$–$C_4$-alkylcarbonylamino, $C_1$–$C_4$-alkoxycarbonylamino, $C_1$–$C_4$-alkylamino-carbonylamino, di-($C_1$–$C_4$-alkyl)-amino-carbonylamino, or the radical $-CO-R^6$, or R³ and R⁴ furthermore represent $C_1$–$C_4$-alkylsulphonyloxy, di-($C_1$–$C_4$-alkyl)-aminosulphonylamino or the radical $-CH=N-R^7$, in which p represents the numbers 1 or 2 and R⁵ represents $C_1$–$C_4$-alkyl which is optionally substituted by fluorine, chlorine, bromine, cyano or $C_1$–$C_4$-alkoxycarbonyl, or R⁵ represents $C_1$–$C_4$-alkoxy, $C_1$–$C_4$-alkoxy-$C_1$–$C_4$-alkylamino or di($C_1$–$C_4$-alkyl)-amino, R⁶ represents $C_1$–$C_6$-alkyl, $C_1$–$C_6$-alkoxy which is optionally substituted by fluorine, chlorine, methoxy or ethoxy; $C_3$–$C_6$-cycloalkoxy, $C_3$–$C_6$-alkenyloxy, $C_1$–$C_4$-alkylthio, amino, $C_1$–$C_4$-alkylamino, $C_1$–$C_4$-alkoxyamino, $C_1$–$C_4$-alkoxy-$C_1$–$C_4$-alkyl-amino or di-($C_1$–$C_4$-alkyl)amino which are optionally substituted by fluorine or chlorine and R⁷ represents $C_1$–$C_6$-alkyl which is optionally substituted by fluorine, chlorine, cyano, carboxyl, $C_1$–$C_4$-alkoxy, $C_1$–$C_4$-alkylthio, $C_1$–$C_4$-alkylsulphinyl or $C_1$–$C_4$-alkylsulphonyl, benzyl which is optionally substituted by fluorine or chlorine, $C_3$–$C_6$-alkenyl or $C_3$–$C_6$-alkynyl which are optionally substituted by fluorine or chlorine, phenyl which is optionally substituted by fluorine, chlorine, bromine, $C_1$–$C_4$-alkyl, $C_1$–$C_4$-alkoxy, trifluoromethylthio, $C_1$–$C_6$-alkoxy, $C_3$–$C_6$-alkenyloxy, $C_3$–$C_6$-alkynyloxy or benzyloxy which are optionally substituted by fluorine or chlorine, or R⁷ furthermore represents amino, $C_1$–$C_4$-alkylamino, di($C_1$–$C_4$-alkyl)-amino, phenylamino, $C_1$–$C_4$-alkyl-carbonylamino, $C_1$–$C_4$-alkoxycarbonylamino, $C_1$–$C_4$-alkyl-sulphonylamino or phenyl sulphonylamino which is optionally substituted by fluorine, chlorine, bromine or methyl, R¹⁰ and R¹¹ are identical or different and represent hydrogen, fluorine, chlorine, bromine, nitro, cyano, or $C_1$–$C_4$-alkyl which is optionally substituted by fluorine or chlorine; $C_2$-$C_4$-alkenyl which is optionally substituted by fluorine or chlorine, $C_1$-$C_4$-alkoxy which is optionally substituted by fluorine or chlorine; $C_1$-$C_4$-alkylthio, $C_1$-$C_4$-alkylsulphinyl or $C_1$-$C_4$-alkylsulphonyl which are optionally substituted by fluorine or chlorine; and di-($C_1$-$C_4$-alkyl)-aminosulphonyl, $C_1$-$C_4$-alkoxycarbonyl, dimethylaminocarbonyl or dioxolanyl; or a salt thereof.

4. A salt of a compound according to claim 1, with the hydroxide, hydride, amide or carbonate or sodium potassium or calcium, the $C_1$-$C_4$-alkoxide of sodium or potassium, ammonia, an $C_1$-$C_4$-alkylamine, di-($C_1$-$C_4$-alkyl)-amine or tri-($C_1$-$C_4$-alkyl)-amine.

5. A sulphonylated carboxamide according to claim 1, in which
$R^2$ represents the radical

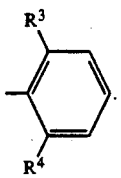

6. A sulphonylated carboxamide according to claim 5, in which $R^4$ is hydrogen.

7. A compound according to claim 1, wherein such compound is N-(2-methoxycarbonyl-phenylsulphonyl)-5-methyl-isoxazole-3-carboxamide of the formula

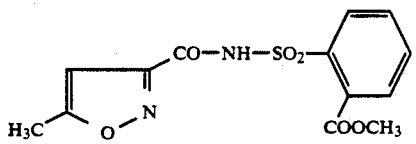

or a salt thereof.

8. A herbicidal composition comprising a herbicidally effective amount of a compound of salt according to claim 1 and a diluent.

9. A method of combating unwanted vegetation which comprises applying to such vegetation or to a locus from which it is desired to exclude such vegetation a herbicidally effective amount of a compound or salt according to claim 7.

10. A sulphonylated carboxamide of the formula

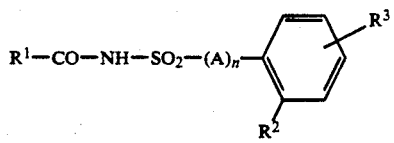

in which
n represents the numbers 0 or 1,
A represents oxygen, imino (NH) or methylene ($CH_2$),
$R^1$ represents a five-membered heteroaryl radical from the group consisting of oxazolyl, isoxazolyl, thiazolyl, isothiazolyl, oxadiazolyl and thiadiazolyl, which is optionally monosubstituted or polysubstituted by identical or different halogen or by optionally halogen-substituted $C_1$-$C_6$-alkyl, phenyl, $C_1$-$C_6$-alkoxy, $C_1$-$C_6$-alkylthio, $C_1$-$C_6$-alkylsulphinyl, $C_1$-$C_6$-alkylsulphonyl, $C_1$-$C_6$-alkylamino or di-($C_1$-$C_4$-alkyl)-amino, and
$R^2$ represents fluorine, chlorine, bromine, iodine, cyano, nitro, carboxyl, $C_1$-$C_4$-alkyl, $C_1$-$C_4$-alkoxy, $C_1$-$C_4$-alkylthio, phenyl, $C_1$-$C_4$-alkylsulphinyl, $C_1$-$C_4$-alkylsulphonyl, di-($C_1$-$C_4$-alkyl)-aminosulphonyl, or the radical —$S(O)_p$—$R^5$,
p represents the numbers 1 or 2 and
$R^5$ represents $C_1$-$C_4$-alkoxy-$C_1$-$C_4$-alkylamino which are optionally substituted by fluorine or chlorine, furthermore represents $C_1$-$C_4$-alkoxycarbonyl, which is optionally substituted by fluorine, chlorine, or $C_1$-$C_4$-alkoxy,
$R^3$ represents hydrogen, fluorine, chlorine, bromine, methyl, or a salt thereof, with the exclusion of the compound 2-(dimethylamino)-N-[(4-methylphenyl) sulphonyl]-5-thiazole carboxamide.

11. A compound according to claim 1, wherein such compound is N-(2-methoxycarbonyl-phenylsulphonyl)-3-methyl-1,2,4-oxadiazole-5-carboxamide of the formula

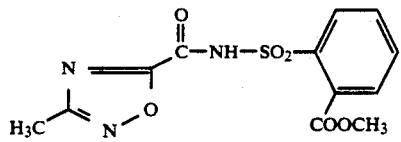

* * * * *